United States Patent
Carter et al.

(10) Patent No.: US 8,217,055 B2
(45) Date of Patent: Jul. 10, 2012

(54) PYRIDO-PYRAZINE DERIVATIVES USEFUL AS HERBICIDAL COMPOUNDS

(75) Inventors: Neil Brian Carter, Bracknell (GB); Matthew Robert Cordingley, Bracknell (GB); Patrick Jelf Crowley, Bracknell (GB); Michael Drysdale Turnbull, Bracknell (GB)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 12/518,923

(22) PCT Filed: Dec. 6, 2007

(86) PCT No.: PCT/GB2007/004662
§ 371 (c)(1), (2), (4) Date: Mar. 9, 2010

(87) PCT Pub. No.: WO2008/071918
PCT Pub. Date: Jun. 19, 2008

(65) Prior Publication Data
US 2010/0167929 A1    Jul. 1, 2010

(30) Foreign Application Priority Data

Dec. 12, 2006 (GB) .................................. 0624760.5

(51) Int. Cl.
*A61K 31/44* (2006.01)

(52) U.S. Cl. ...................................... 514/303; 544/350

(58) Field of Classification Search .................. 514/303; 544/350
See application file for complete search history.

(56) References Cited

U.S. PATENT DOCUMENTS
5,491,126 A    2/1996    Selby

FOREIGN PATENT DOCUMENTS
| WO | 2005/010000 A | 2/2005 |
| WO | 2005/123698 A | 12/2005 |

*Primary Examiner* — James O Wilson
*Assistant Examiner* — Douglas M Willis
(74) *Attorney, Agent, or Firm* — James Cueva

(57) ABSTRACT

The present invention relates to compounds of formula (I):

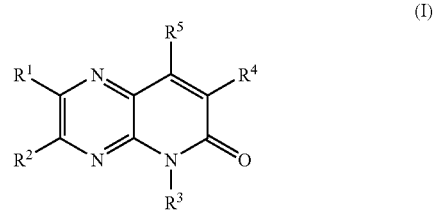

(I)

wherein $R^1$, $R^2$, $R^3$, $R^4$ and $R^5$ are as defined in claim 1; or a salt or N-oxide thereof.
Furthermore, the present invention relates to processes for preparing compounds of formula (I), to methods of controlling plants and compositions comprising compounds of formula (I).

28 Claims, No Drawings

PYRIDO-PYRAZINE DERIVATIVES USEFUL AS HERBICIDAL COMPOUNDS

The present invention relates to novel, herbicidal 5-haloalkyl-5H-pyrido[2,3-b]pyrazin-6-ones and 5-haloalkenyl-5H-pyrido[2,3-b]pyrazin-6-ones, to processes for their preparation, to compositions comprising those compounds, and to their use in controlling plants or in inhibiting plant growth.

Pyrido[2,3-b]pyrazines were disclosed as intermediates in the synthesis of fungicidal compounds, for example, in WO 04/056825, WO 05/123698 and WO 05/123733. Pyrido[2,3-b]pyrazines were disclosed as fungicidal compounds in WO 05/010000.

It has now surprisingly been found that certain 5-haloalkyl-5H-pyrido[2,3-b]pyrazin-6-ones and 5-haloalkenyl-5H-pyrido[2,3-b]pyrazin-6-ones display excellent herbicidal and growth-inhibiting properties.

The present invention therefore provides a compound of formula (I)

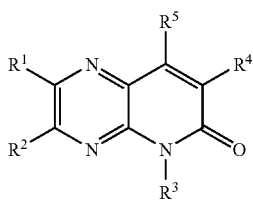

wherein
$R^1$ and $R^2$ are independently hydrogen, $C_1$-$C_4$alkyl, $C_1$-$C_4$haloalkyl, halo, cyano, hydroxy, $C_1$-$C_4$alkoxy, $C_1$-$C_4$alkylthio, aryl or aryl substituted by one to five $R^6$, which may be the same or different, or heteroaryl or heteroaryl substituted by one to five $R^6$, which may be the same or different;
$R^3$ is $C_1$-$C_4$haloalkyl, $C_2$-$C_4$haloalkenyl or $C_2$-$C_4$haloalkynyl;
$R^4$ is aryl or aryl substituted by one to five $R^8$, which may be the same or different, or heteroaryl or heteroaryl substituted by one to four $R^8$, which may be the same or different;
$R^5$ is hydroxy or a group which can be metabolised to the hydroxy group;
each $R^6$ and $R^8$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, $C_1$-$C_{10}$alkylcarbonylamino-, aryl or aryl substituted by one to three $R^{13}$, which may be the same or different, heteroaryl or heteroaryl substituted by one to three $R^{13}$, which may be the same or different, aryl-$C_1$-$C_4$alkyl- or aryl-$C_1$-$C_4$alkyl- wherein the aryl moiety is substituted by one to three $R^{13}$, which may be the same or different, heteroaryl-$C_1$-$C_4$alkyl- or heteroaryl-$C_1$-$C_4$alkyl- wherein the heteroaryl moiety is substituted by one to three $R^{13}$, which may be the same or different, aryloxy- or aryloxy- substituted by one to three $R^{13}$, which may be the same or different, heteroaryloxy- or heteroaryloxy- substituted by one to three $R^{13}$, which may be the same or different, arylthio- or arylthio- substituted by one to three $R^{13}$, which may be the same or different, or heteroarylthio- or heteroarylthio- substituted by one to three $R^{13}$, which may be the same or different; and
each $R^{13}$ is independently halo, cyano, nitro, $C_1$-$C_6$alkyl, $C_1$-$C_6$haloalkyl or $C_1$-$C_6$alkoxy; or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

For example, a compound of formula (Ia), i.e. a compound of formula (I) wherein $R^5$ is as defined for compounds of formula (I) other than hydroxy, can be drawn in only one tautomeric form.

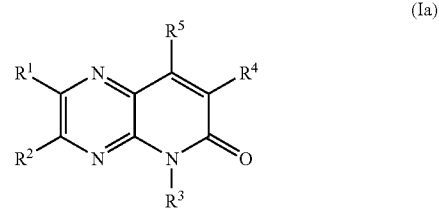

Whereas a compound of formula (Ib), i.e. a compound of formula (I) wherein $R^5$ is hydroxy, can be drawn in three tautomeric forms.

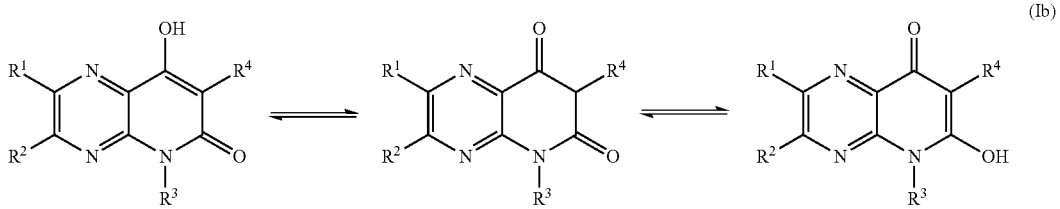

Each alkyl moiety (either alone or as part of a larger group, such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tent-butyl or neo-pentyl. The alkyl groups are preferably $C_1$-$C_6$ alkyl groups, more preferably $C_1$-$C_4$ and most preferably $C_1$-$C_3$ alkyl groups.

Alkenyl and alkynyl moieties (either alone or as part of a larger group, such as alkenyloxy or alkynyloxy) can be in the form of straight or branched chains, and the alkenyl moieties, where appropriate, can be of either the (E)- or (Z)-configuration. Examples are vinyl, allyl, prop-2-enyl and propargyl. The alkenyl and alkynyl groups are preferably $C_2$-$C_6$ alkenyl or alkynyl groups, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CHF_2$, —$CH_2CF_3$ or —$CH_2CHF_2$. Haloalkenyl and haloalkynyl groups (either alone or as part of a larger group, such as haloalkenyloxy or haloalkynyloxy) are alkenyl and alkynyl groups, respectively, which are substituted with one or more of the same or different halogen atoms and are, for example, —CH=$CF_2$, —CCl=CClF or —C≡CCl.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methylcyclopropyl, 2-methylcyclopropyl, cyclobutyl, cyclopentyl and cyclohexyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred heteroaryl group is pyridine. Examples of bicyclic groups are benzothiophenyl, benzimidazolyl, benzothiadiazolyl, quinolinyl, cinnolinyl, quinoxalinyl and pyrazolo[1,5-a]pyrimidinyl.

The term "heterocyclyl" is defined to include heteroaryl and in addition their unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation. The term "metabolism" as used herein means the conversion or breakdown of a substance from one form to another by a living organism, in particular in a plant (in planta).

Preferred values of $R^1$, $R^2$, $R^3$, $R^4$, $R^5$, $R^6$, $R^8$, $R^9$, $R^{10}$, $R^{11}$, $R^{12}$, $R^{13}$ and $R^{14}$ are, in any combination, as set out below.

Preferably $R^1$ is hydrogen, $C_1$-$C_4$alkyl, $C_1$-$C_4$haloalkyl, halo, cyano, hydroxy or $C_1$-$C_4$alkoxy.

More preferably $R^1$ is hydrogen, $C_1$-$C_4$allyl, halo, cyano or hydroxy.

Even more preferably $R^1$ is hydrogen, methyl, chloro or bromo.

Yet even more preferably $R^1$ is hydrogen or chloro.

Most preferably $R^1$ is hydrogen.

Preferably $R^2$ is hydrogen, $C_1$-$C_4$alkyl, $C_1$-$C_4$haloalkyl, halo, cyano, hydroxy or $C_1$-$C_4$alkoxy.

More preferably $R^2$ is hydrogen, $C_1$-$C_4$alkyl, halo, cyano or hydroxy.

Even more preferably $R^2$ is hydrogen, methyl, chloro or bromo.

Yet even more preferably $R^2$ is hydrogen or chloro.

Most preferably $R^2$ is hydrogen.

Preferably $R^3$ is $C_1$-$C_4$haloalkyl or $C_2$-$C_4$haloalkenyl. Examples of such preferred groups for $R^3$ are 2-fluoro-ethyl, 2,2-difluoro-ethyl, 2,2,2-trifluoro-ethyl, 3-chloro-propyl, 3,3,3-trifluoro-propyl, 4-chloro-butyl, 4,4,4,3,3-pentafluoro-butyl, 2-chloro-prop-2-en-1-yl, 3,3-dichloro-prop-2-en-1-yl, 2-fluoro-prop-2-en-1-yl, 3,3-difluoro-prop-2-en-1-yl, 4,4-difluoro-but-3-en-1-yl and 3,4,4-trifluoro-but-3-en-1-yl.

More preferably $R^3$ is $C_1$-$C_3$haloalkyl, in particular where the halogen atoms are fluorine. Examples of such more preferred groups for $R^3$ are 2-fluoro-ethyl, 2,2-difluoro-ethyl, 2,2,2-trifluoro-ethyl and 3,3,3-trifluoro-propyl.

Even more preferably $R^3$ is $C_1$-$C_2$haloalkyl, in particular where the halogen atoms are fluorine. Examples of such even more preferred groups for $R^3$ are 2-fluoro-ethyl, 2,2-difluoro-ethyl and 2,2,2-trifluoro-ethyl.

Most preferably $R^3$ is 2,2-difluoro-ethyl.

Preferably $R^4$ is aryl or aryl substituted by one to five $R^8$, which may be the same or different. Examples of such preferred groups for $R^4$ are 2,5-bis-(trifluoromethyl)-phenyl, 3-bromo-2-chloro-6-fluoro-phenyl, 2-bromo-4-fluoro-phenyl, 5-bromo-2-methoxy-phenyl, 2-bromo-phenyl, 2-bromo-4-trifluoromethyl-phenyl, 2-chloro-3,6-difluoro-5-nitro-phenyl, 2-chloro-3,6-difluoro-phenyl, 2-chloro-4,5-difluoro-phenyl, 2-chloro-6-fluoro-3-methyl-phenyl, 2-chloro-6-fluoro-5-methyl-phenyl, 2-chloro-6-fluoro-3-nitro-phenyl, 2-chloro-4-fluoro-phenyl, 2-chloro-5-fluoro-phenyl, 2-chloro-6-fluoro-phenyl, 2-chloro-phenyl, 3-chloro-phenyl, 4-chloro-phenyl, 2-chloro-3-trifluoromethyl-phenyl, 2-chloro-5-trifluoromethyl-phenyl, 5-chloro-2-trifluoromethyl-phenyl, 2-chloro-6-trifluoromethyl-phenyl, 2,3-dichloro-6-fluoro-phenyl, 2,4-dichloro-5-fluoro-phenyl, 3,5-dichloro-2-methoxy-phenyl, 2,3-dichloro-phenyl, 2,4-dichloro-phenyl, 2,5-dichloro-phenyl, 2,6-dichloro-phenyl, 3,4-dichloro-phenyl, 2,6-dichloro-4-trifluoromethoxy-phenyl, 2,6-dichloro-4-trifluoromethyl-phenyl, 2,6-diethyl-4-methyl-phenyl, 2-difluoromethoxy-phenyl, 4,5-difluoro-2-methoxy-phenyl, 2,3-dimethoxy-phenyl, 2,4-dimethoxy-phenyl, 2,5-dimethyl-phenyl, 2-ethyl-phenyl, 2-fluoro-phenyl, 4-fluoro-2-trifluoromethyl-phenyl, 6-fluoro-2-trifluoromethyl-phenyl, 2-iodo-phenyl, 2-methoxy-phenyl, 2-methoxy-5-trifluoromethoxy-phenyl, 6-methyl-2-nitro-phenyl, 2-methyl-phenyl, naphth-2-yl, naphth-3-yl, phenyl, 2-nitro-4-trifluoromethyl-phenyl, 2,3,5-trichloro-phenyl, 2,3,6-trichloro-phenyl, 2-trifluoromethoxy-phenyl, 2-trifluoromethyl-phenyl, 2,3,6-trifluoro-phenyl and 2,4,6-trimethyl-phenyl.

More preferably $R^4$ is aryl substituted by one to four $R^8$, which may be the same or different. Examples of such more preferred groups for $R^4$ are 2,5-bis-(trifluoromethyl)-phenyl, 3-bromo-2-chloro-6-fluoro-phenyl, 2-chloro-3,6-difluoro-phenyl, 2-chloro-4-fluoro-phenyl, 2-chloro-5-fluoro-phenyl, 2-chloro-phenyl, 2-chloro-3-trifluoromethyl-phenyl, 2-chloro-5-trifluoromethyl-phenyl, 2-chloro-6-trifluoromethyl-phenyl, 2,3-dichloro-6-fluoro-phenyl, 2,4-dichloro-5-fluoro-phenyl, 3,5-dichloro-2-methoxy-phenyl, 2,3-dichloro-phenyl, 2,4-dichloro-phenyl, 2,5-dichloro-phenyl, 2,6-dichloro-phenyl, 2,6-dichloro-4-trifluoromethoxy-phenyl, 2,6-dichloro-4-trifluoromethyl-phenyl, 2,6-diethyl-4-methyl-phenyl, 2,3-dimethoxy-phenyl, 2-fluoro-phenyl, 2-methoxy-phenyl, 2-methoxy-5-trifluoromethoxy-phenyl, 2,3,6-trichloro-phenyl, 2-trifluoromethoxy-phenyl, 2-trifluoromethyl-phenyl and 2,4,6-trimethyl-phenyl.

Most preferably $R^4$ is aryl substituted by two to three $R^8$, which may be the same or different. Examples of such most preferred groups for $R^4$ are 2,5-bis-(trifluoromethyl)-phenyl, 3-bromo-2-chloro-6-fluoro-phenyl, 2-chloro-3,6-difluoro-phenyl, 2-chloro-5-fluoro-phenyl, 2-chloro-5-trifluoromethyl-phenyl, 2-chloro-6-trifluoromethyl-phenyl, 2,3-dichloro-6-fluoro-phenyl, 2,6-dichloro-phenyl, 2,6-dichloro-4-trifluoromethoxy-phenyl and 2,3,6-trichloro-phenyl.

In one preferred embodiment $R^4$ is 2,5-bis-(trifluoromethyl)-phenyl.

In one preferred embodiment $R^4$ is 3-bromo-2-chloro-6-fluoro-phenyl.

In one preferred embodiment $R^4$ is 2-chloro-3,6-difluoro-phenyl.

In one preferred embodiment $R^4$ is 2-chloro-5-fluoro-phenyl.

In one preferred embodiment $R^4$ is 2-chloro-5-trifluoromethyl-phenyl.

In one preferred embodiment $R^4$ is 2-chloro-6-trifluoromethyl-phenyl.

In one preferred embodiment $R^4$ is 2,3-dichloro-6-fluoro-phenyl.

In one preferred embodiment $R^4$ is 2,6-dichloro-phenyl.

In one preferred embodiment $R^4$ is 2,6-dichloro-4-trifluoromethoxy-phenyl.

In one preferred embodiment $R^4$ is 2,3,6-trichloro-phenyl.

Preferably $R^5$ is hydroxy, $R^9$-oxy-, $R^{10}$-carbonyloxy-, tri-$R^{11}$-silyloxy- or $R^{12}$-sulfonyloxy-, wherein $R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy;

$R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, $C_1$-$C_{10}$alkylthio-, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy- substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio- or heteroarylthio- substituted by one to three $R^{14}$, which may be the same or different;

each $R^{11}$ is independently $C_1$-$C_{10}$alkyl or phenyl or phenyl substituted by one to five substituents independently selected from halo, cyano, nitro, $C_1$-$C_6$alkyl, $C_1$-$C_6$haloalkyl or $C_1$-$C_6$alkoxy;

$R^{12}$ is $C_1$-$C_{10}$alkyl, $C_1$-$C_{10}$haloalkyl, or phenyl or phenyl substituted by one to five substituents independently selected from halo, cyano, nitro, $C_1$-$C_6$alkyl, $C_1$-$C_6$haloalkyl or $C_1$-$C_6$alkoxy; and each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_4$haloalkylthio-, $C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy.

More preferably $R^5$ is hydroxy, $R^9$-oxy- or $R^{10}$-carbonyloxy-.

Even more preferably $R^5$ is hydroxy, $C_1$-$C_4$alkoxy, $C_1$-$C_4$alkylcarbonyloxy-, $C_3$-$C_6$cycloalkylcarbonyloxy-, $C_3$-$C_{10}$cycloalkyl-$C_1$-$C_{10}$alkylcarbonyloxy-, $C_1$-$C_4$haloalkyl-carbonyloxy-, $C_2$-$C_4$alkenylcarbonyloxy-, $C_2$-$C_4$alkynylcarbonyloxy-, $C_1$-$C_4$alkoxy-$C_1$-$C_4$alkylcarbonyloxy-, $C_1$-$C_4$alkylthio-$C_1$-$C_4$alkylcarbonyloxy-, $C_1$-$C_4$alkoxycarbonyloxy-, $C_2$-$C_4$alkenyloxycarbonyloxy-, $C_2$-$C_4$alkynyloxycarbonyloxy-, $C_1$-$C_4$alkylthiocarbonyloxy-, N—$C_1$-$C_4$alkyl-aminocarbonyloxy-, N,N-di-($C_1$-$C_4$alkyl)-aminocarbonyloxy-, aryl-carbonyloxy- or arylcarbonyloxy- substituted by one to three $R^{14}$, which may be the same or different, heteroarylcarbonyloxy- or heteroarylcarbonyloxy- substituted by one to three $R^{14}$, which may be the same or different, aryl-$C_1$-$C_4$alkylcarbonyloxy- or aryl-$C_1$-$C_4$alkylcarbonyloxy- wherein the aryl moiety is substituted by one to three $R^{14}$, which may be the same or different, heteroaryl-$C_1$-$C_4$alkylcarbonyloxy- or heteroaryl-$C_1$-$C_4$alkylcarbonyloxy- wherein the heteroaryl moiety is substituted by one to three $R^{14}$, which may be the same or different, aryloxycarbonyloxy- or aryloxycarbonyloxy-substituted by one to three $R^{14}$, which may be the same or different, heteroaryloxycarbonyloxy- or heteroaryloxycarbonyloxy- substituted by one to three $R^{14}$, which may be the same or different, arylthiocarbonyloxy- or arylthiocarbonyloxy-substituted by one to three $R^{14}$, which may be the same or different, or heteroarylthio-carbonyloxy- or heteroarylthiocarbonyloxy- substituted by one to three $R^{14}$, which may be the same or different. Examples of preferred groups for $R^5$ are hydroxy, methoxy, ethoxy, methylcarbonyloxy-, ethylcarbonyloxy-, iso-propylcarbonyloxy-, n-propyl-carbonyloxy-, but-2-ylcarbonyloxy-, 2-methyl-propylcarbonyloxy-, tert-butylcarbonyl-oxy-, cyclopropylcarbonyloxy-, cyclopentylmethylcarbonyloxy-, chloromethylcarbonyl-oxy-, trifluoromethylcarbonyloxy-, allylcarbonyloxy-, (E)-prop-1-en-1-ylcarbonyloxy-, 2-methyl-prop-1-en-1-ylcarbonyloxy-, methoxymethylcarbonyloxy-, ethoxycarbonyloxy-, tert-butoxycarbonyloxy-, but-2-yn-1-yloxycarbonyloxy-, ethylthiocarbonyloxy-, N,N-diethylaminocarbonyloxy-, phenylcarbonyloxy-, 3-methoxy-phenylcarbonyloxy-, 4-nitrophenylcarbonyloxy-, benzylcarbonyloxy-, furan-2-ylcarbonyloxy-, 2,5-dimethyl-furan-3-ylcarbonyloxy-, thiophen-2-ylcarbonyloxy-, 3,5-dimethyl-isoxazol-4-ylcarbonyl-oxy-, and 1-phenyl-prop-1-ylcarbonyloxy-.

Yet even more preferably $R^5$ is hydroxy, $C_1$-$C_4$alkylcarbonyloxy-, $C_3$-$C_6$cyclo-alkylcarbonyloxy-, $C_2$-$C_4$alkenylcarbonyloxy-, $C_2$-$C_4$alkynylcarbonyloxy-, $C_1$-$C_4$alkoxy-carbonyloxy-, $C_2$-$C_4$alkenyloxycarbonyloxy-, $C_2$-$C_4$alkynyloxycarbonyloxy- or $C_1$-$C_4$alkylthiocarbonyloxy-. Examples of more preferred groups for $R^5$ are hydroxy, methylcarbonyloxy-, ethylcarbonyloxy-, iso-propylcarbonyloxy-, n-propylcarbonyloxy-, but-2-ylcarbonyloxy-, 2-methyl-propylcarbonyloxy-, tert-butylcarbonyloxy-, cyclo-propylcarbonyloxy-, allylcarbonyloxy-, (E)-prop-1-en-1-ylcarbonyloxy-, 2-methyl-prop-1-en-1-ylcarbonyloxy-, ethoxycarbonyloxy-, tert-butoxycarbonyloxy-, but-2-yn-1-yloxy-carbonyloxy-, and ethylthiocarbonyloxy-.

Most preferably $R^5$ is hydroxy, $C_1$-$C_4$alkylcarbonyloxy-, $C_1$-$C_4$alkoxycarbonyl-oxy- or $C_1$-$C_4$alkylthiocarbonyloxy-. Examples of most preferred groups for $R^5$ are hydroxy, methylcarbonyloxy-, ethylcarbonyloxy-, iso-propylcarbonyloxy-, n-propyl-carbonyloxy-, but-2-ylcarbonyloxy-, 2-methyl-propylcarbonyloxy-, tert-butylcarbonyl-oxy-, ethoxycarbonyloxy-, tert-butoxycarbonyloxy-, and ethylthiocarbonyloxy-.

In one preferred embodiment $R^5$ is hydroxy.

In one preferred embodiment $R^5$ is $R^9$-oxy-, wherein $R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy. Such $R^5$ groups may be metabolised, preferably in planta, to give the corresponding compound wherein $R^5$ is hydroxy.

In one preferred embodiment $R^5$ is $R^{10}$-carbonyloxy-, wherein $R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy- substituted by one to three $R^{14}$, which may be the same or different, heteroaryloxy- or heteroaryloxy- substituted by one to three $R^{14}$, which may be the same or different, arylthio- or arylthio- substituted by one to three $R^{14}$, which may be the same or different, or heteroarylthio- or heteroarylthio-substituted by one to three $R^{14}$, which may be the same or different; and each $R^{14}$ is independently halo, cyano, nitro, $C_1$-$C_{10}$alkyl, $C_1$-$C_4$haloalkyl, $C_1$-$C_{10}$alkoxy. $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy. Such $R^5$ groups may be metabolised, preferably in planta, to give the corresponding compound wherein $R^5$ is hydroxy.

In one preferred embodiment $R^5$ is iso-propylcarbonyloxy- or tert-butyl-carbonyloxy-.

In one preferred embodiment $R^5$ is $C_1$-$C_4$alkylsulfonyloxy-. Examples of such preferred groups for $R^5$ are methylsulfonyloxy- and iso-propylsulfonyloxy-.

In one preferred embodiment $R^5$ is tri-($C_1$-$C_4$alkyl)-silyloxy-. An example of a preferred group for $R^5$ is dimethyl-tent-butyl-silyloxy-.

Preferably each $R^6$ is independently halo, $C_1$-$C_4$alkyl, $C_1$-$C_4$haloalkyl, $C_1$-$C_4$alkoxy or $C_1$-$C_4$haloalkoxy. Examples of such preferred groups for $R^6$ are chloro, fluoro, methyl, ethyl, trifluoromethyl, methoxy or trifluoromethoxy.

Preferably each $R^8$ is independently halo, cyano, nitro, $C_1$-$C_{10}$alkyl, $C_r$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl- or $C_1$-$C_4$haloalkylsulfonyl-.

More preferably each $R^8$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio or $C_1$-$C_4$haloalkylthio. Examples of such more preferred groups for $R^8$ are iodo, bromo, chloro, fluoro, cyano, nitro, methyl, ethyl, trifluoromethyl, methoxy, methoxycarbonyl, trifluoromethoxy or trifluoromethylthio.

Most preferably each $R^8$ is independently halo, $C_1$-$C_{10}$alkyl, $C_1$-$C_4$haloalkyl, $C_1$-$C_{10}$alkoxy or $C_1$-$C_4$haloalkoxy. Examples of such most preferred groups for $R^8$ are bromo, chloro, fluoro, methyl, ethyl, trifluoromethyl, methoxy or trifluoromethoxy.

In one embodiment, $R^9$ is preferably $C_1$-$C_{10}$alkyl, more preferably $C_1$-$C_4$alkyl, even more preferably methyl or ethyl, most preferably methyl.

In another embodiment, $R^9$ is preferably $C_2$-$C_{10}$alkenyl, $C_2$-$C_{10}$alkynyl, aryl-$C_1$-$C_4$alkyl- or aryl-$C_1$-$C_4$alkyl- wherein the aryl moiety is substituted by one to three $R^{13}$, which may be the same or different, more preferably $C_3$-$C_4$alkenyl, or $C_3$-$C_4$alkynyl, benzyl or benzyl wherein the phenyl moiety is substituted by one to three $R^{13}$, which may be the same or different, even more preferably allyl, propargyl or benzyl, most preferably $R^9$ is allyl.

Preferably $R^{10}$ is $C_1$-$C_{10}$alkyl, $C_3$-$C_{10}$cycloalkyl, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_1$-$C_{10}$alkylthio-, N—$C_1$-$C_4$alkyl-amino-, N,N-di-($C_1$-$C_4$alkyl)-amino-, phenyl or phenyl substituted by one to three $R^{14}$, which may be the same or different, benzyl or benzyl wherein the phenyl moiety is substituted by one to three $R^{14}$, which may be the same or different, thienyl or thienyl substituted by one to three $R^{14}$, which may be the same or different, pyridyl or pyridyl substituted by one to three $R^{14}$, which may be the same or different, phenoxy or phenoxy substituted by one to three $R^{14}$, which may be the same or different, or phenylthio or phenylthio substituted by one to three $R^{14}$, which may be the same or different.

Most preferably $R^{10}$ is iso-propyl or tent-butyl.

Preferably each $R^{11}$ is independently $C_1$-$C_4$alkyl.

Preferably $R^{12}$ is $C_1$-$C_4$alkyl or $C_1$-$C_4$haloalkyl.

Preferably each $R^{13}$ is independently halo, nitro, $C_1$-$C_4$alkyl, $C_1$-$C_4$haloalkyl or $C_1$-$C_4$alkoxy. Examples of such preferred groups are chloro, fluoro, nitro, methyl, ethyl, trifluoromethyl and methoxy.

Preferably each $R^{14}$ is independently halo, nitro, $C_1$-$C_4$alkyl, $C_1$-$C_4$haloalkyl, $C_4$alkoxy or $C_1$-$C_4$haloalkoxy. Examples of such preferred groups are chloro, fluoro, nitro, methyl, ethyl, trifluoromethyl, methoxy and trifluoromethoxy.

More preferably each $R^{14}$ is independently halo, $C_1$-$C_4$alkyl, $C_1$-$C_4$haloalkyl or $C_1$-$C_4$alkoxy.

The compounds in Tables 1 to 27 below illustrate the compounds of the invention.

TABLE 1

Table 1 provides 30 compounds of formula (I), where $R^1$ and $R^2$ are both hydrogen, $R^4$ is 2-chloro-3,6-difluoro-phenyl and $R^3$ and $R^5$ have the values listed in Table 1.

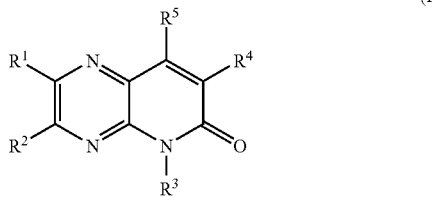

(I)

| Compound number | $R^3$ | $R^5$ |
|---|---|---|
| 1.001 | 2,2-difluoro-ethyl | —OH |
| 1.002 | 2,2-difluoro-ethyl | —OCH$_3$ |
| 1.003 | 2,2-difluoro-ethyl | —OCOCH$_3$ |
| 1.004 | 2,2-difluoro-ethyl | —OCOCH$_2$CH$_3$ |
| 1.005 | 2,2-difluoro-ethyl | —OCOCH(CH$_3$)$_2$ |
| 1.006 | 2,2-difluoro-ethyl | —OCOC(CH$_3$)$_3$ |
| 1.007 | 2,2-difluoro-ethyl | —OCO-cyclo-C$_3$H$_5$ |
| 1.008 | 2,2-difluoro-ethyl | —OCO—C$_6$H$_5$ |
| 1.009 | 2,2-difluoro-ethyl | —OCOCH$_2$C$_6$H$_5$ |
| 1.010 | 2,2-difluoro-ethyl | —OCOCH$_2$Cl |
| 1.011 | 2,2-difluoro-ethyl | —OCOCF$_3$ |
| 1.012 | 2,2-difluoro-ethyl | —OCOCH$_2$OCH$_3$ |
| 1.013 | 2,2-difluoro-ethyl | —OCON(CH$_3$CH$_2$)$_2$ |
| 1.014 | 2,2-difluoro-ethyl | —O(CO)OCH$_2$CH$_3$ |
| 1.015 | 2,2-difluoro-ethyl | —O(CO)SCH$_2$CH$_3$ |
| 1.016 | 2,2,2-trifluoro-ethyl | —OH |
| 1.017 | 2,2,2-trifluoro-ethyl | —OCH$_3$ |
| 1.018 | 2,2,2-trifluoro-ethyl | —OCOCH$_3$ |
| 1.019 | 2,2,2-trifluoro-ethyl | —OCOCH$_2$CH$_3$ |
| 1.020 | 2,2,2-trifluoro-ethyl | —OCOCH(CH$_3$)$_2$ |
| 1.021 | 2,2,2-trifluoro-ethyl | —OCOC(CH$_3$)$_3$ |
| 1.022 | 2,2,2-trifluoro-ethyl | —OCO-cyclo-C$_3$H$_5$ |
| 1.023 | 2,2,2-trifluoro-ethyl | —OCO—C$_6$H$_5$ |
| 1.024 | 2,2,2-trifluoro-ethyl | —OCOCH$_2$C$_6$H$_5$ |
| 1.025 | 2,2,2-trifluoro-ethyl | —OCOCH$_2$Cl |
| 1.026 | 2,2,2-trifluoro-ethyl | —OCOCF$_3$ |
| 1.027 | 2,2,2-trifluoro-ethyl | —OCOCH$_2$OCH$_3$ |
| 1.028 | 2,2,2-trifluoro-ethyl | —OCON(CH$_3$CH$_2$)$_2$ |
| 1.029 | 2,2,2-trifluoro-ethyl | —O(CO)OCH$_2$CH$_3$ |
| 1.030 | 2,2,2-trifluoro-ethyl | —O(CO)SCH$_2$CH$_3$ |

Table 2:
Table 2 provides 30 compounds of formula (I), where $R^1$ and $R^2$ are both hydrogen, $R^4$ is 2-chloro-4-fluoro-phenyl and $R^3$ and $R^5$ have the values listed in Table 1.

Table 3:
Table 3 provides 30 compounds of formula (I), where $R^1$ and $R^2$ are both hydrogen, $R^4$ is 2-chloro-phenyl and $R^3$ and $R^5$ have the values listed in Table 1.

Table 4:
Table 4 provides 30 compounds of formula (I), where $R^1$ and $R^2$ are both hydrogen, $R^4$ is 3,5-dichloro-2-methoxy-phenyl and $R^3$ and $R^5$ have the values listed in Table 1.

Table 5:
Table 5 provides 30 compounds of formula (I), where $R^1$ and $R^2$ are both hydrogen, $R^4$ is 2,3-dichloro-phenyl and $R^3$ and $R^5$ have the values listed in Table 1.

Table 6:
Table 6 provides 30 compounds of formula (I), where $R^1$ and $R^2$ are both hydrogen, $R^4$ is 2,4-dichloro-phenyl and $R^3$ and $R^5$ have the values listed in Table 1.

Table 7:
Table 7 provides 30 compounds of formula (I), where $R^1$ and $R^2$ are both hydrogen, $R^4$ is 2,5-dichloro-phenyl and $R^3$ and $R^5$ have the values listed in Table 1.

Table 8:
Table 8 provides 30 compounds of formula (I), where $R^1$ and $R^2$ are both hydrogen, $R^4$ is 2,6-dichloro-phenyl and $R^3$ and $R^5$ have the values listed in Table 1.

Table 9:
Table 9 provides 30 compounds of formula (I), where $R^1$ and $R^2$ are both hydrogen, $R^4$ is 2,6-dichloro-4-trifluoromethyl-phenyl and $R^3$ and $R^5$ have the values listed in Table 1.

Table 10:
Table 10 provides 30 compounds of formula (I), where $R^1$ and $R^2$ are both hydrogen, $R^4$ is 2,6-diethyl-4-methyl-phenyl and $R^3$ and $R^5$ have the values listed in Table 1.

Table 11:
Table 11 provides 30 compounds of formula (I), where $R^1$ and $R^2$ are both hydrogen, $R^4$ is 2-fluoro-phenyl and $R^3$ and $R^5$ have the values listed in Table 1.

Table 12:
Table 12 provides 30 compounds of formula (I), where $R^1$ and $R^2$ are both hydrogen, $R^4$ is 2-methoxy-phenyl and $R^3$ and $R^5$ have the values listed in Table 1.

Table 13:
Table 13 provides 30 compounds of formula (I), where $R^1$ and $R^2$ are both hydrogen, $R^4$ is 2-trifluoromethoxy-phenyl and $R^3$ and $R^5$ have the values listed in Table 1.

Table 14:
Table 14 provides 30 compounds of formula (I), where $R^1$ and $R^2$ are both hydrogen, $R^4$ is 2-trifluoromethyl-phenyl and $R^3$ and $R^5$ have the values listed in Table 1.

Table 15:
Table 15 provides 30 compounds of formula (I), where $R^1$ and $R^2$ are both hydrogen, $R^4$ is 3-bromo-2-chloro-6-fluoro-phenyl and $R^3$ and $R^5$ have the values listed in Table 1.

Table 16:
Table 16 provides 30 compounds of formula (I), where $R^1$ and $R^2$ are both hydrogen, $R^4$ is 2,3-dichloro-6-fluoro-phenyl and $R^3$ and $R^5$ have the values listed in Table 1.

Table 17:
Table 17 provides 30 compounds of formula (I), where $R^1$ and $R^2$ are both hydrogen, $R^4$ is 2,6-dichloro-4-trifluoromethoxy-phenyl and $R^3$ and $R^5$ have the values listed in Table 1.

Table 18:
Table 18 provides 30 compounds of formula (I), where $R^1$ and $R^2$ are both hydrogen, $R^4$ is 2-chloro-6-trifluoromethyl-phenyl and $R^3$ and $R^5$ have the values listed in Table 1.

Table 19:
Table 19 provides 30 compounds of formula (I), where $R^1$ and $R^2$ are both hydrogen, $R^4$ is 2-chloro-5-trifluoromethyl-phenyl and $R^3$ and $R^5$ have the values listed in Table 1.

Table 20:
Table 20 provides 30 compounds of formula (I), where $R^1$ and $R^2$ are both hydrogen, $R^4$ is 2-chloro-5-fluoro-phenyl and $R^3$ and $R^5$ have the values listed in Table 1.

Table 21:
Table 21 provides 30 compounds of formula (I), where $R^1$ and $R^2$ are both hydrogen, $R^4$ is 2,4-dichloro-5-fluoro-phenyl and $R^3$ and $R^5$ have the values listed in Table 1.

Table 22:
Table 22 provides 30 compounds of formula (I), where $R^1$ and $R^2$ are both hydrogen, $R^4$ is 2-methoxy-5-trifluoromethoxy-phenyl and $R^3$ and $R^5$ have the values listed in Table 1.

Table 23:
Table 23 provides 30 compounds of formula (I), where $R^1$ and $R^2$ are both hydrogen, $R^4$ is 2,3-dimethoxy-phenyl and $R^3$ and $R^5$ have the values listed in Table 1.

Table 24:
Table 24 provides 30 compounds of formula (I), where $R^1$ and $R^2$ are both hydrogen, $R^4$ is 2-chloro-3-trifluoromethyl-phenyl and $R^3$ and $R^5$ have the values listed in Table 1.
Table 25:
Table 25 provides 30 compounds of formula (I), where $R^1$ and $R^2$ are both hydrogen, $R^4$ is 2,4,6-trimethyl-phenyl and $R^3$ and $R^5$ have the values listed in Table 1.
Table 26:
Table 26 provides 30 compounds of formula (I), where $R^1$ and $R^2$ are both hydrogen, $R^4$ is 2,5-bis-(trifluoromethyl)-phenyl and $R^3$ and $R^5$ have the values listed in Table 1.
Table 27:
Table 27 provides 30 compounds of formula (I), where $R^1$ and $R^2$ are both hydrogen, $R^4$ is 2,3,6-trichloro-phenyl and $R^3$ and $R^5$ have the values listed in Table 1.

The compounds of the invention may be made by a variety of methods, for example by the methods described in Schemes 1 to 14.

suitable solvent, such as dichloro-methane, or other amide coupling methods which have been reviewed in Tetrahedron (2005), 61(46), 10827-10852.

2) Compounds of formula (5) wherein $R^1$, $R^2$ and $R^4$ are as defined for a compound of formula (I) can be prepared by treating a compound of formula (4) as defined in 1) with a base in a suitable solvent, such as potassium carbonate in N,N-dimethylformamide or lithium hexamethyldisilazide in tetrahydrofuran, optionally using microwave heating.

3) Compounds of formula (6) wherein $R^1$, $R^2$, $R^4$ and $R^{10}$ are as defined for a compound of formula (I) can be prepared by reaction of a compound of formula (5) as defined in 2) with an acid chloride of formula $R^{10}COCl$ or an acid anhydride of formula $(R^{10}CO)_2O$ wherein $R^{10}$ is as defined for a compound of formula (I), optionally in the presence of a base, such as triethylamine or pyridine, optionally in a suitable solvent, such as dichloromethane.

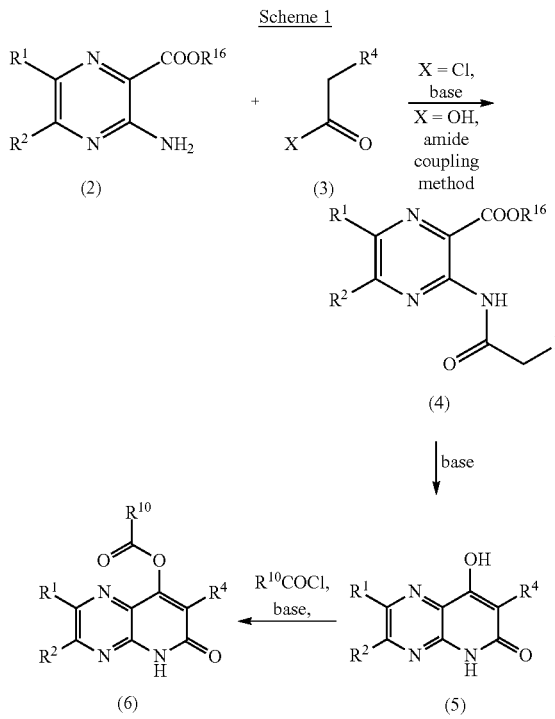

Scheme 1

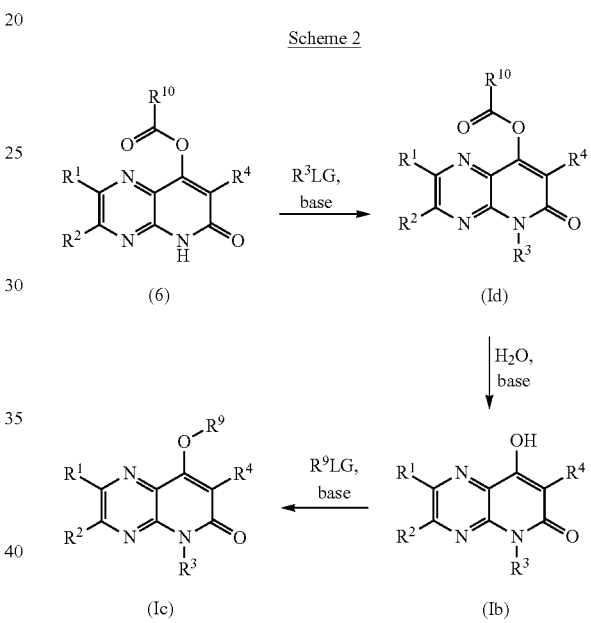

Scheme 2

1) Compounds of formula (4) wherein $R^1$, $R^2$ and $R^4$ are as defined for a compound of formula (I) and $R^{16}$ is $C_1$-$C_6$alkyl can be made by reaction of an amino-pyrazine ester of formula (2) wherein $R^1$ and $R^2$ are as defined for a compound of formula (I) and $R^{16}$ is $C_1$-$C_6$alkyl with an acid derivative of formula (3) wherein $R^4$ is as defined for a compound of formula (I) and X is halogen or hydroxy, as shown in Scheme 1. For example, if (3) is an acid chloride (i.e. where X is chlorine) the reaction can conveniently be carried out optionally in the presence of a base, such as triethylamine or pyridine, in a suitable solvent, such as acetonitrile or dichloromethane, optionally using microwave heating. Alternatively, if (3) is a carboxylic acid (i.e. where X is hydroxy) the reaction can conveniently be carried out using an amide coupling method, for example by reaction with a coupling agent, such as bis(2-oxo-3-oxazolidinyl)phosphinic chloride, in the presence of a base, such as triethylamine, in a 4) Compounds of formula (Id), i.e. a compound of formula (I) wherein $R^5$ is —O—CO—$R^{10}$, can be prepared from a compound of formula (6) as defined in 3) by reaction with a compound of formula $R^3LG$ wherein $R^3$ is as defined for a compound of formula (I) and LG is a leaving group such as a halide, for example bromide or iodide, or tosylate, mesylate or triflate, in the presence of a base, such as potassium carbonate, optionally in the presence of an activator/iodide, such as potassium iodide, in a suitable solvent, such as acetonitrile or N,N-dimethylformamide, optionally using microwave heating, as shown in Scheme 2.

5) Compounds of formula (Ib), i.e. a compound of formula (I) wherein $R^5$ is hydroxy, can be prepared by treating a compound of formula (Id) as defined in 4) with a base, such as sodium hydroxide or potassium carbonate, and water in a suitable solvent, such as methanol or N,N-dimethylformamide.

6) Compounds of formula (Ic), i.e. a compound of formula (I) wherein $R^5$ is —O—$R^9$, can be prepared from a compound of formula (Ib) as defined in 5) by reaction with a compound of formula $R^9LG$ wherein $R^9$ is as defined for a compound of formula (I) and LG is a leaving group such as halide, for example bromide or iodide, or tosylate, mesylate or triflate, in the presence of a base, such as potassium carbonate, in a suitable solvent, such as N,N-dimethylformamide.

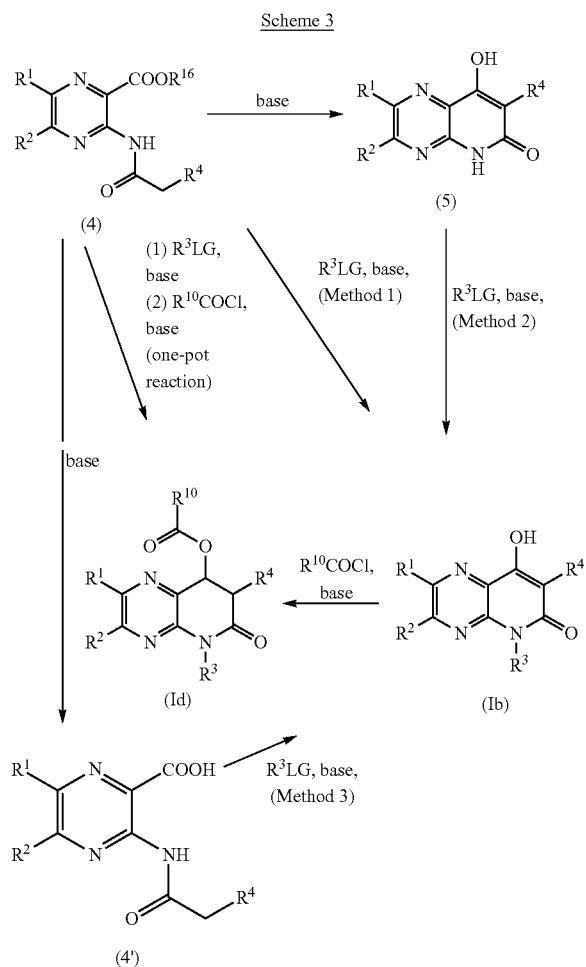

10) Compounds of formula (Ib) as defined in 5) can also be made from a compound of formula (5) as defined in 2) by reaction with a compound of formula $R^3LG$ as defined in 4), in the presence of a base, such as potassium hexamethyldisilazide, in a suitable solvent, such as tetrahydrofuran, optionally using microwave heating (Method 2). The synthesis of compounds of formula (5) was described under 2).

11) Compounds of formula (Ib) as defined in 5) can also be made by reaction of a compound of formula (4') with a compound of formula $R^3LG$ as defined in 4), in the presence of a base, such as sodium hexamethyldisilazide, in a suitable solvent, such as tetrahydrofuran, optionally using microwave heating (Method 3). Compounds of formula (4') can be made from a compound of formula (4) by reaction with a base, such as lithium hexamethyldisilazide, in a suitable solvent, such as tetrahydrofuran or N,N-dimethyl-formamide, optionally using microwave heating.

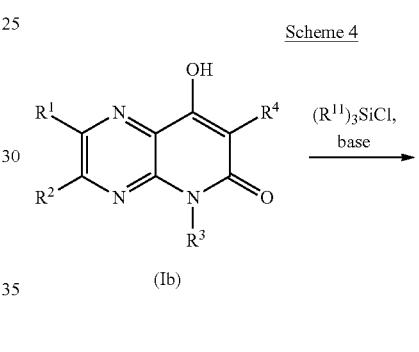

7) Compounds of formula (Id) as defined in 4) can additionally be prepared in a shortened route directly from a compound of formula (4) as defined in 1) by reaction with a compound of formula $R^3LG$ as defined in 4), in the presence of a base, such as sodium or potassium hexamethyldisilazide, in a suitable solvent, such as tetrahydrofuran, optionally using microwave heating, followed by reaction with an acid chloride of formula $R^{10}COCl$ or an acid anhydride of formula $(R^{10}CO)_2O$ as defined in 3), optionally in the presence of a base, such as triethylamine, in the same reaction pot, as shown in Scheme 3.

8) Alternatively compounds of formula (Id) as defined in 4) can be made from a compound of formula (Ib) as defined in 5), by reaction with an acid chloride of formula $R^{10}COCl$ or an acid anhydride of formula $(R^{10}CO)_2O$ as defined in 3), optionally in the presence of a base, such as triethylamine, optionally in a suitable solvent, such as dichloromethane.

9) Compounds of formula (Ib) as defined in 5) can be made by reaction of a compound of formula (4) as defined in 1) with a compound of formula $R^3LG$ as defined in 4), in the presence of a base, such as potassium hexamethyldisilazide, in a suitable solvent, such as tetrahydrofuran, optionally using microwave heating (Method 1).

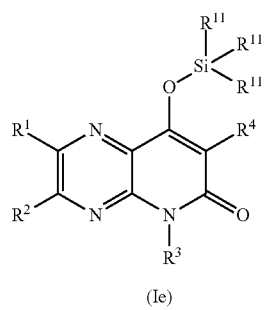

12) Silyl compounds of formula (Ie), i.e. a compound of formula (I) wherein $R^5$ is $—O—Si(R^{11})_3$, can be made from a compound of formula (Ib) as defined in 5), by reaction with a trialkylsilyl chloride of formula $(R^{11})_3SiCl$, in a suitable solvent, such as tetrahydrofuran or acetonitrile, in the presence of a base, such as triethylamine, as shown in Scheme 4.

Scheme 5

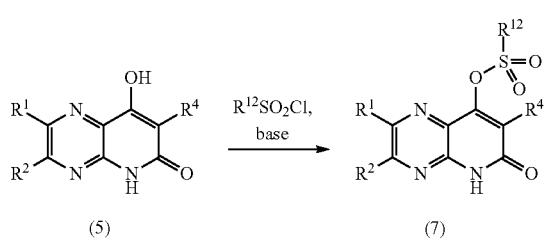

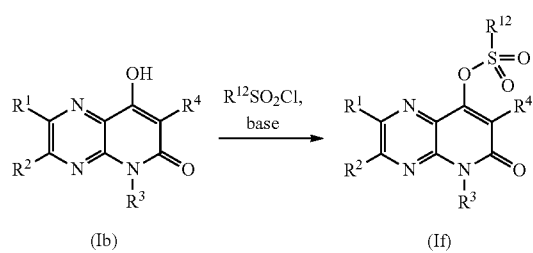

13) Sulfonyl compounds of formula (7) wherein $R^1$, $R^2$, $R^4$ and $R^{12}$ are as defined for a compound of formula (I) can be made from a compound of formula (5) as defined in 2) by reaction with a sulfonyl chloride of formula $R^{12}SO_2Cl$ wherein $R^{12}$ is as defined for a compound of formula (I), in the presence of a base, such as triethylamine, in a suitable solvent, such as tetrahydrofuran or dichloromethane, as shown in Scheme 5.

14) Sulfonyl compounds of formula (If), i.e. a compound of formula (I) wherein $R^5$ is $-O-SO_2-R^{12}$, can be made by reaction of a compound of formula (7) as defined in 13), with a compound of formula $R^3LG$ as defined in 4), in the presence of a base, such as sodium or potassium hexamethyldisilazide, in a suitable solvent, such as tetrahydro-furan, optionally using microwave heating.

15) Alternatively, compounds of formula (If) as defined in 14) can be made by reaction of a compound of formula (Ib) as defined in 5) with a sulfonyl chloride of formula $R^{12}SO_2Cl$ as defined in 13), in the presence of a base, such as triethylamine, in a suitable solvent, such as tetrahydrofuran or dichloromethane.

Scheme 6

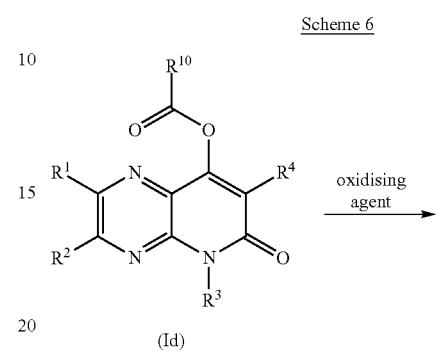

16) A mixture of N-oxides of formula (Ig), i.e. a compound of formula (I) wherein the 5-nitrogen is oxidised, and $R^5$ is $-O-CO-R^{10}$, and N-oxides of formula (Ih), i.e. a compound of formula (I) wherein the 5-nitrogen is oxidised, and $R^5$ is hydroxy, can be made by reaction of a compound of formula (Id) as defined in 4), with an oxidising agent, for example a per-acid, such as per-trifluoroacetic acid, generated in situ for example by trifluoroacetic anhydride and hydrogen peroxide on urea pellets, in a suitable solvent, such as dichloromethane, as shown in Scheme 6.

Scheme 7

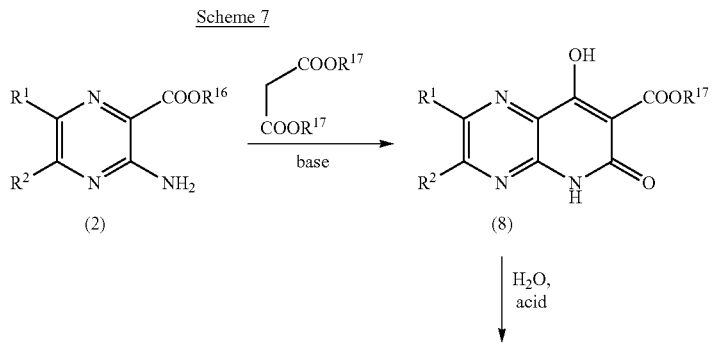

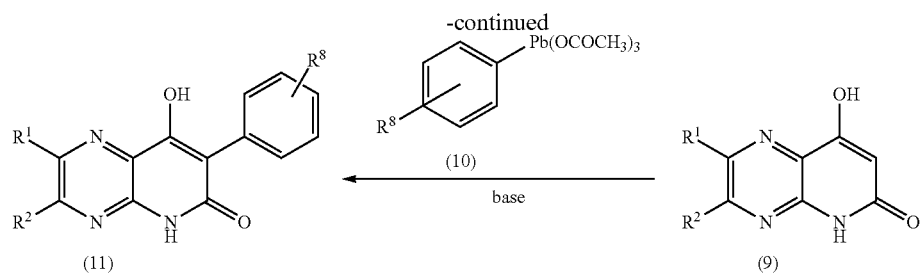

17) Compounds of formula (8) wherein $R^1$ and $R^2$ are as defined for a compound of formula (I) and $R^{17}$ is $C_1$-$C_6$alkyl can be made by reaction of an aminopyrazine ester of formula (2) as defined under 1) with a dialkyl malonate of formula $CH_2(CO_2R^{17})_2$ wherein $R^{17}$ is $C_1$-$C_6$alkyl, in the presence of a base, such as sodium methoxide, in a suitable solvent, such as methanol, at a temperature of 20° C. to reflux, preferably at reflux, as shown in Scheme 7.

18) Compounds of formula (9) wherein $R^1$ and $R^2$ are as defined for a compound of formula (I) can be made by hydrolysis and decarboxylation of a compound of formula (8) as defined in 17) by treatment with strong aqueous acid, for example concentrated hydrochloric acid, or alternatively by treatment with dilute aqueous acid, for example dilute hydrochloric acid, and water in a suitable solvent, such as ethanol, optionally using microwave heating.

19) Compounds of formula (11) wherein $R^1$, $R^2$ and $R^8$ are as defined for a compound of formula (I) can be made by reaction of a compound of formula (9) as defined in 18) with a lead compound of formula (10) wherein $R^8$ is as defined for a compound of formula (I), in the presence of a base, such as 4-dimethylaminopyridine, and in a suitable solvent, such as dimethyl sulfoxide. Lead compounds (10) are known in the literature and can be made by the methods as described in Aust. J. Chem., 1979, 32, 1561-6; and J. Chem. Soc. Perkin Trans. 1, 1990, 3, 715-20.

Scheme 8

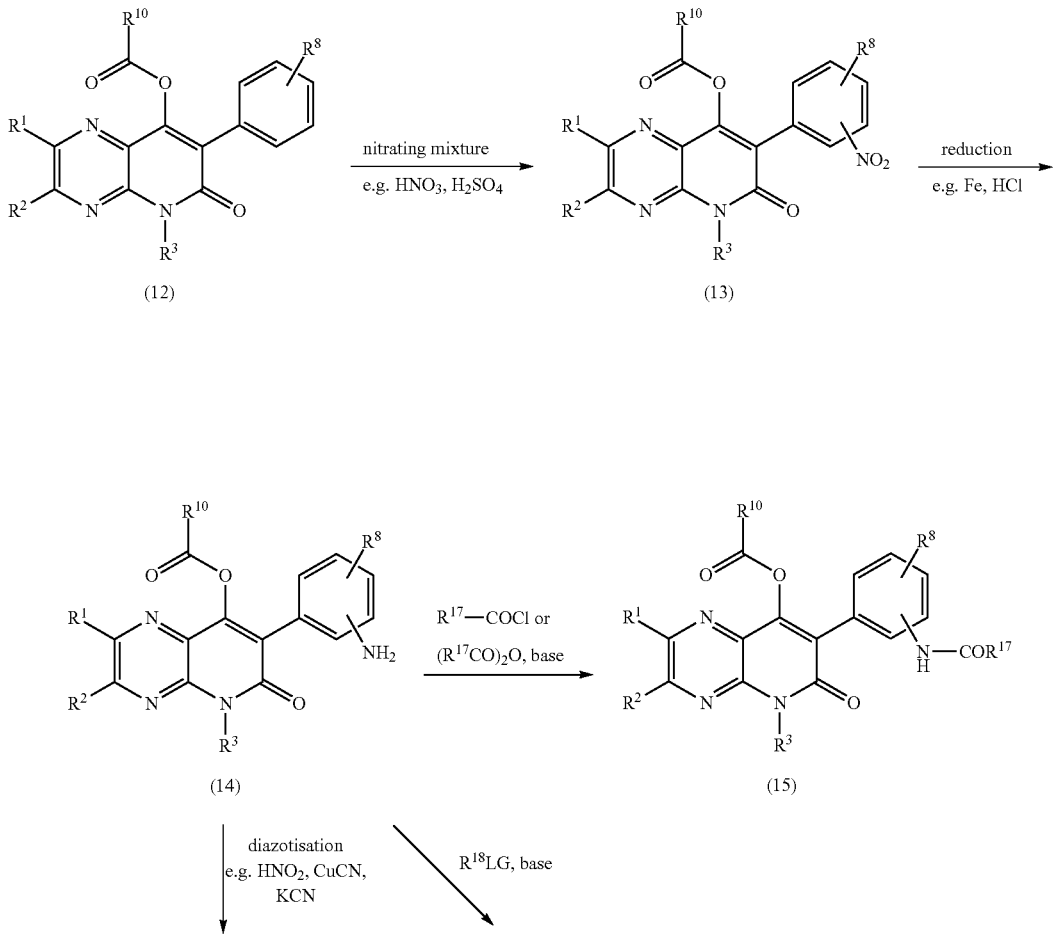

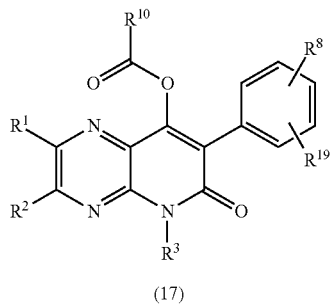
(17)

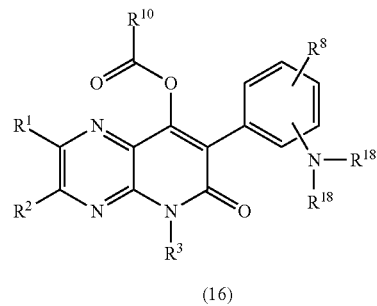
(16)

20) Nitro compounds of formula (13) wherein $R^1$, $R^2$, $R^3$, $R^8$ and $R^{10}$ are as defined for a compound of formula (I), can be made by nitration of a compound of formula (12) wherein $R^1$, $R^2$, $R^3$, $R^8$ and $R^{10}$ are as defined for a compound of formula (1), with a nitration mixture, for example fuming nitric acid and concentrated sulfuric acid, as shown in Scheme 8.

21) Amino compounds of formula (14) wherein $R^1$, $R^2$, $R^3$, $R^8$ and $R^{10}$ are as defined for a compound of formula (I), can be made by reduction of a compound of formula (13) as defined in 20), using standard reducing conditions, for example, iron filings in aqueous hydrochloric acid.

22) Acylated compounds of formula (15) wherein $R^1$, $R^2$, $R^3$, $R^8$ and $R^{10}$ are as defined for a compound of formula (I) and $R^{17}$ is as defined in 17), can be made by acylation of a compound of formula (14) as defined in 21), for example by reaction with an acid chloride of formula $R^{17}COCl$ or an acid anhydride $(R^{17}CO)_2O$ wherein $R^{17}$ is as defined in 17), in the presence of a base, such as triethylamine, in a suitable solvent, such as dichloromethane.

23) Alkylated compounds of formula (16) wherein $R^1$, $R^2$, $R^3$, $R^8$ and $R^{10}$ are as defined for a compound of formula (I) and $R^{18}$ is $C_1$-$C_6$alkyl, can be made by alkylation of a compound of formula (14) as defined in 21), for example by reaction with a compound of formula $R^{18}LG$, wherein $R^{18}$ is $C_1$-$C_6$alkyl and LG is a leaving group such as a halide, for example bromide or iodide, or tosylate, mesylate or triflate, optionally in the presence of a base, such as potassium carbonate, in a suitable solvent, such as ethanol or toluene.

24) Compounds of formula (17) wherein $R^1$, $R^2$, $R^3$, $R^8$ and $R^{10}$ are as defined for a compound of formula (I) and $R^{19}$ is cyano, $C_1$-$C_4$alkylthio, halo, or hydroxy, can be made by reaction of a compound of formula (14) as defined in 21), by diazotisation, for example by reaction with an alkyl nitrite, in the presence of a suitable nucleophile, for example potassium cyanide, in the presence of a copper salt, for example cuprous cyanide, in a suitable solvent, such as acetonitrile.

Scheme 9

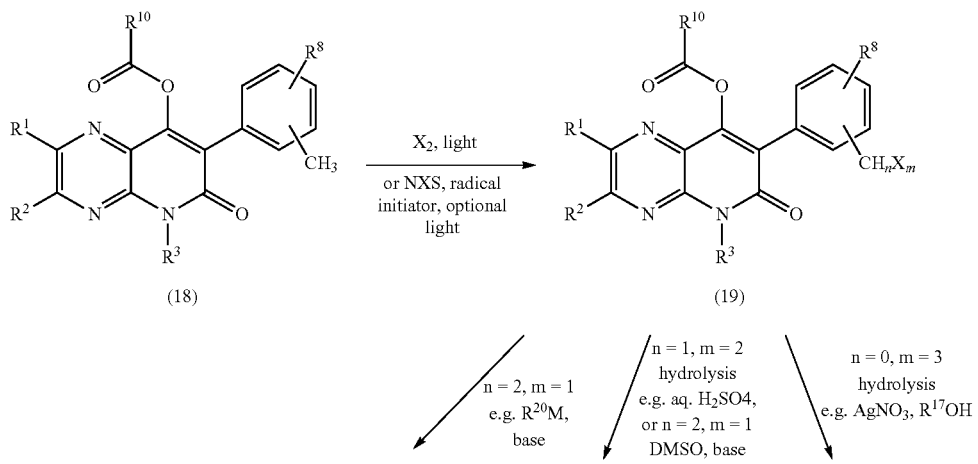

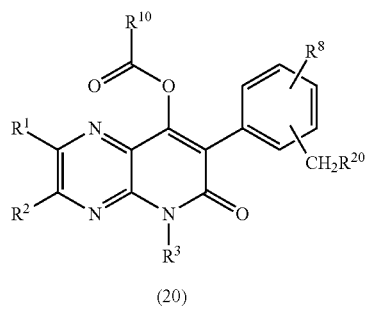 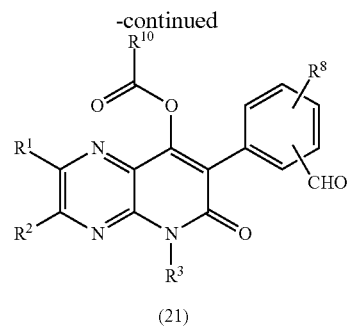 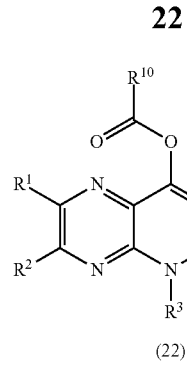

(20)　　　　　(21)　　　　　(22)

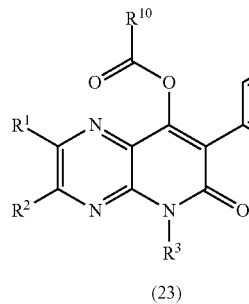 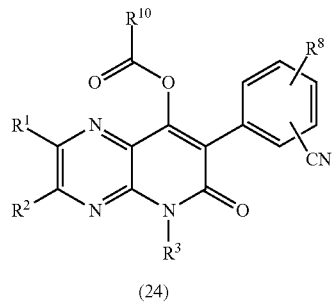

(23)　　　　　(24)

25) Haloalkyl compounds of formula (19) wherein $R^1$, $R^2$, $R^3$, $R^8$ and $R^{10}$ are as defined for a compound of formula (I), X is a halogen and n+m=3, can be made by reaction of a compound of formula (18) with a halogenation agent, such as halogen of formula $X_2$ wherein X is chlorine or bromine, in the presence of light, or a N-halosuccinimide of formula

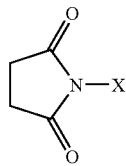

wherein X is chlorine, bromine or iodine, in the presence of a radical initiator, such as benzoyl peroxide, in a suitable solvent, such as carbon tetrachloride, and optionally in the presence of a light source, such as a 500 watt tungsten halogen lamp, at reflux, as shown in Scheme 9.

26) Compounds of formula (20) wherein $R^1$, $R^2$, $R^3$, $R^8$ and $R^{10}$ are as defined for a compound of formula (I) and $R^{20}$ is $C_1$-$C_8$alkoxy, $C_1$-$C_8$thioalkoxy, optionally substituted phenoxy, optionally substituted thiophenoxy, cyano, hydroxy, $C_1$-$C_4$alkyl-amino or di-($C_1$-$C_4$alkyl)amino, can be made by reaction of a compound of formula (19) as defined in 25) wherein n=2 and m=1, with a compound of formula $R^{20}$H wherein $R^{20}$ is $C_1$-$C_8$alkoxy, $C_1$-$C_8$thioalkoxy, optionally substituted phenoxy, optionally substituted thiophenoxy, a mono-($C_1$-$C_4$alkyl)amine or a di-($C_1$-$C_4$alkyl)amine, in the presence of a base, such as potassium carbonate or sodium hydride, in a suitable solvent, such as ethanol or N,N-dimethylformamide, or with a compound of formula $R^{20}$M wherein $R^{20}$ is cyano and M is a metal, such as sodium, or wherein $R^{20}$ is hydroxy and M is a metal, such as sodium, in a suitable solvent, such as ethanol or N,N-dimethylformamide.

27) Aldehydes of formula (21) wherein $R^1$, $R^2$, $R^3$, $R^8$ and $R^{10}$ are as defined for a compound of formula (I) can be made from a compound of formula (19) as defined in 25) where n=1 and m=2, by hydrolysis with an acid, for example aqueous sulfuric acid, or from a compound of formula (19) as defined in 25) where n=2 and m=1, by reaction with dimethylsulfoxide in the presence of a base, such as potassium carbonate.

28) Compounds of formula (22) wherein $R^1$, $R^2$, $R^3$, $R^8$ and $R^{10}$ are as defined for a compound of formula (I) and $R^{17}$ is as defined in 17), can be made from a compound of formula (19) as defined in 25) where n=0 and m=3, by hydrolysis with an alcohol of formula $R^{17}$OH wherein $R^{17}$ is as defined in 17), optionally in the presence of a silver salt, such as silver nitrate.

29) Compounds of formula (23) wherein $R^1$, $R^2$, $R^3$, $R^8$ and $R^{10}$ are as defined for a compound of formula (I) and $R^{21}$ is $C_1$-$C_8$alkyl or optionally substituted benzyl can be made from an aldehyde of formula (21) as defined in 27) by reaction with a hydroxyl-amine $R^{21}$O—$NH_2$ or its salt wherein $R^{21}$ is $C_1$-$C_8$alkyl or optionally substituted benzyl, for example the hydrochloride salt, optionally in the presence of a base, such as sodium acetate, in a suitable solvent, such as ethanol.

30) Compounds of formula (24) wherein $R^1$, $R^2$, $R^3$, $R^8$, $R^{10}$ are as defined for a compound of formula (I), can be made from a compound of formula (23) as defined in 29) in the particular case where $R^{21}$ is hydrogen, by reaction with a dehydrating agent, such as acetic anhydride.

Scheme 10

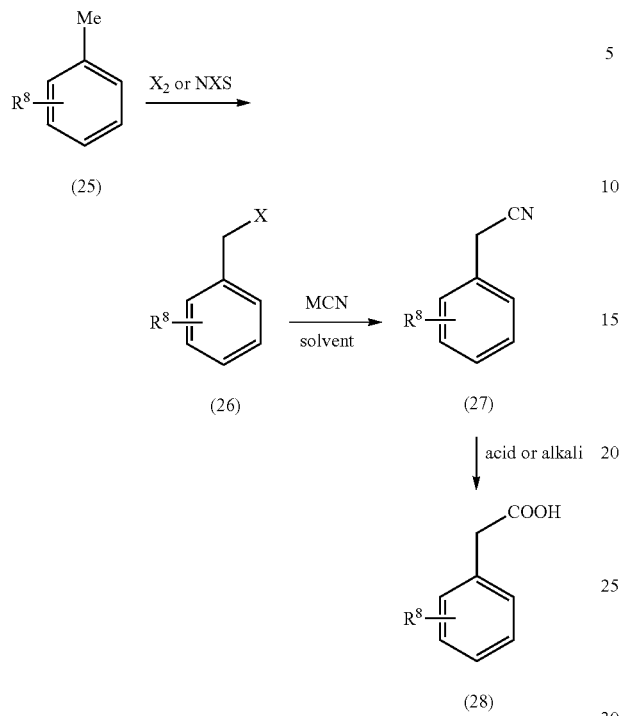

Scheme 11

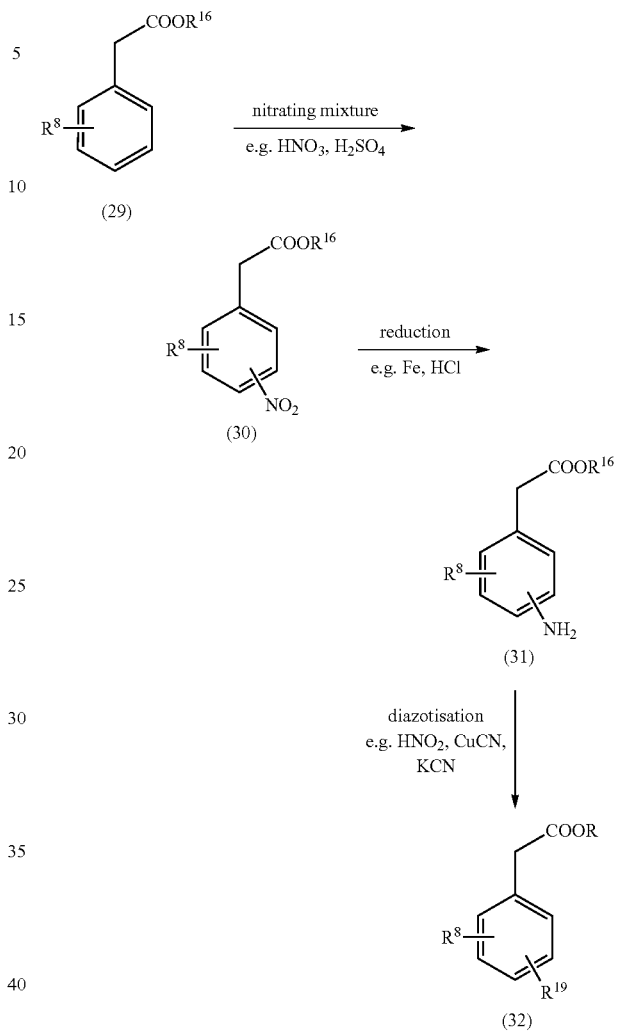

31) In certain cases where aryl acetic acids are not commercially available it is necessary to make them. A typical synthesis is shown in Scheme 10. Benzyl halides of formula (26) wherein $R^8$ is as defined for a compound of formula (I) and X is halogen, can be made by reaction of a substituted toluene of formula (25) wherein $R^8$ is as defined for a compound of formula (I), with a halogenation agent, such as halogen of formula $X_2$ wherein X is chlorine or bromine, in the presence of light, or a N-halosuccinimide of formula

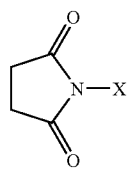

wherein X is chlorine, bromine or iodine, in the presence of a radical initiator, such as benzoyl peroxide, in a suitable solvent, such as carbon tetrachloride, and optionally in the presence of a light source, such as a 500 watt tungsten halogen lamp, at reflux.

32) Benzyl cyanides of formula (27) wherein $R^8$ is as defined for a compound of formula (I) can be made by reaction of a compound of formula (26) as defined in 31) with a metal cyanide, such as potassium cyanide, in a suitable solvent, such as ethanol, at reflux.

33) Phenyl acetic acids of formula (28) wherein $R^8$ is as defined for a compound of formula (I) can be made by reaction of a compound of formula (27) as defined in 32) by hydrolysis using aqueous acid or alkali, but preferably aqueous acid, such as aqueous sulfuric acid, at reflux.

34) Nitro compounds of formula (30) wherein $R^8$ is as defined for compounds of formula (1) and $R^{16}$ is as defined in 1), can be made by nitration of a compound of formula (29) wherein $R^8$ is as defined for compounds of formula (1) and $R^{16}$ is as defined in 1), with a nitration mixture, for example fuming nitric acid and concentrated sulfuric acid, as shown in Scheme 11.

35) Amino compounds of formula (31) wherein $R^8$ is as defined for compounds of formula (1) and $R^{16}$ is as defined in 1), can be made by reduction of a compound of formula (30) as defined in 34), using standard reducing conditions, for example, iron filings in aqueous hydrochloric acid.

36) Compounds of formula (32) wherein $R^8$ is as defined for compounds of formula (1), $R^{16}$ is as defined in 1), and $R^{19}$ is cyano, $C_1$-$C_4$alkylthio, halo, or hydroxy, can be made by reaction of a compound of formula (31) as defined in 35), by diazotisation, for example by reaction with an alkyl nitrite, in the presence of a suitable nucleophile, for example potassium cyanide, in the presence of a copper salt; for example cuprous cyanide, in a suitable solvent, such as acetonitrile.

Scheme 12

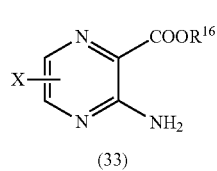

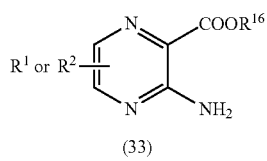

37) Compounds of formula (36) wherein $R^1$ and $R^2$ are as defined for compounds of formula (I) and $R^{16}$ is defined as in 1), can be made from a compound of formula (33) where X is halogen, such as chlorine, bromine or iodine, as shown in Scheme 12. This can be achieved by Suzuki coupling using a boronic acid $R^1B(OH)_2$ or $R^2B(OH)_2$ in the presence of a palladium catalyst, such as palladium(II) acetate, in the presence of a ligand, such as 2'-dicyclohexylphosphino-2,6-dimethoxy-1,1'-biphenyl, in the presence of a base, such as potassium phosphate, in a suitable solvent, such as d mixture of toluene and water, at a temperature of 50° C. to 150° C., preferably of 100° C. to 120° C., optionally using microwave heating. Alternatively, Stille coupling can be used, using a tin reagent $R^1Sn(R^{22})_3$ or $R^2Sn(R^{22})_3$ wherein $R^{22}$ is $C_1$-$C_6$alkyl in the presence of a palladium catalyst, such as palladium(II) chloride, in the presence of a ligand, such as tri-tertiary-butylphosphine, in a suitable solvent, such as N,N-dimethylformamide or acetonitrile, at a temperature of 20° C. to 150° C., preferably of 75° C. to 120° C.

Scheme 13

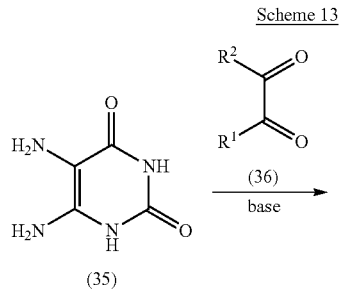

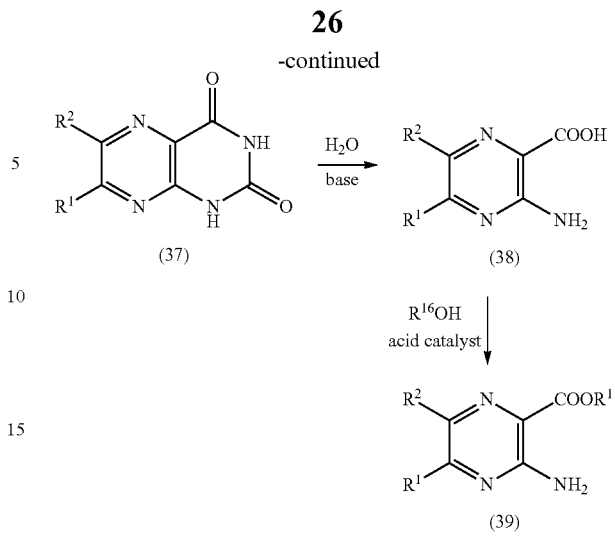

38) Although 3-amino-5-pyrazinecarboxylate esters of formula (39) wherein $R^1$ and $R^2$ are as defined for a compound of formula (I) and $R^{16}$ is as defined in 1), are known in the literature, for example in J. Med. Chem. (1967), 10, 66; J. Med. Chem. (1967), 10, 899; and J. Med. Chem. (1967), 10, 598, there is a need to make these compounds using a shorter or more convenient syntheses. For example, a compound of formula (37) wherein $R^1$ and $R^2$ are as defined for a compound of formula (I), can be synthesised by condensation of diaminouracil of formula (35) or a salt thereof with a diketone or ketoaldehyde of formula (36) wherein $R^1$ and $R^2$ are as defined for a compound of formula (I), in the presence of a base, such as aqueous ammonia.

39) A pyrazine amino acid of formula (38) wherein $R^1$ and $R^2$ are as defined for a compound of formula (I), can be formed by opening the ring of a compound of formula (37) wherein $R^1$ and $R^2$ are as defined for a Compound of formula (I), in the presence of a base, such as sodium hydroxide, and water, optionally using microwave heating.

40) A compound of formula (39) wherein $R^1$ and $R^2$ are as defined for a compound of formula (I) and $R^{16}$ is as defined in 1), can be made from a compound of formula (38) wherein $R^1$ and $R^2$ are as defined for a compound of formula (I), for example by esterification with an alcohol of formula $R^{16}OH$ wherein $R^{16}$ is as defined in 1), such as methanol, in the presence of an acid catalyst, such as acetyl chloride.

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; diallyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood New Jersey, 1981.

Further adjuvants that can usually be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilisers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):

Emulsifiable Concentrates:

| | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |

Dusts:

| | |
|---|---|
| active ingredient: | 0.1 to 10%, preferably 0.1 to 5% |
| solid carrier: | 99.9 to 90%, preferably 99.9 to 99% |

Suspension Concentrates:

| | |
|---|---|
| active ingredient: | 5 to 75%, preferably 10 to 50% |
| water: | 94 to 24%, preferably 88 to 30% |
| surface-active agent: | 1 to 40%, preferably 2 to 30% |

Wettable Powders:

| | |
|---|---|
| active ingredient: | 0.5 to 90%, preferably 1 to 80% |
| surface-active agent: | 0.5 to 20%, preferably 1 to 15% |
| solid carrier: | 5 to 95%, preferably 15 to 90% |

Granules:

| | |
|---|---|
| active ingredient: | 0.1 to 30%, preferably 0.1 to 15% |
| solid carrier: | 99.5 to 70%, preferably 97 to 85% |

The following Examples further illustrate, but do not limit, the invention.

Formulation Examples for Herbicides of Formula (I) (%=% by Weight)

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. CaCO$_3$ or SiO$_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. CaCO$_3$ or SiO$_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention also relates to a method of controlling plants which comprises applying to the plants or to the locus thereof a herbicidally effective amount of a compound of formula I.

The invention also relates to a method of inhibiting plant growth which comprises applying to the plants or to the locus thereof a herbicidally effective amount of a compound of formula I.

The invention also relates to a method of selectively controlling grasses and weeds in crops of useful plants which comprises applying to the useful plants or locus thereof or to the area of cultivation a herbicidally effective amount of a compound of formula I.

Crops of useful plants in which the composition according to the invention can be used include perennial crops, such as citrus fruit, grapevines, nuts, oil palms, olives, pore fruit, stone fruit and rubber, and annual arable crops, such as cereals, for example barley and wheat, cotton, oilseed rape, maize, rice, soy beans, sugar beet, sugar cane, sunflowers, ornamentals and vegetables, especially cereals and maize.

The grasses and weeds to be controlled may be both monocotyledonous species, for example *Agrostis, Alopecurus, Avena, Bromus, Cyperus, Digitaria, Echinochloa, Lolium, Monochoria, Rottboellia, Sagittaria, Scirpus, Setaria, Sida* and *Sorghum*, and dicotyledonous species, for example *Abutilon, Amaranthus, Chenopodium, Chrysanthemum, Galium, Ipomoea, Nasturtium, Sinapis, Solanum, Stellaria, Veronica, Viola* and *Xanthium*.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering.

An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), Nature-Gard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavour).

Areas under cultivation include land on which the crop plants are already growing and land intended for cultivation with those crop plants.

The compounds of formula I according to the invention can also be used in combination with one or more further herbicides. In particular, the following mixtures of the compound of formula I are important:

Mixtures of a compound of formula I with a synthetic auxin (e.g. compound of formula I+clopyralid (162), compound of formula I+2,4-D (211), compound of formula I+dicamba (228), compound of formula I+MCPA (499), compound of formula I+quinclorac (712), or compound of formula I+aminopyralid (CAS RN 150114-71-9)).

Mixtures of a compound of formula I with diflufenzopyr (252).

Mixtures of a compound of formula I with an acetanilide (e.g. compound of formula I+acetochlor (5), compound of formula I+dimethenamid (260), compound of formula I+metolachlor (548), compound of formula I+S-metolachlor (549), or compound of formula I+pretilachlor (656)).

Mixtures of a compound of formula I with flamprop-M (355).

Mixtures of a compound of formula I with flufenacet (BAY FOE 5043) (369).

Mixtures of a compound of formula I with pyroxasulfone (CAS RN 447399-55-5).

Mixtures of a compound of formula I with a triazine (e.g. compound of formula I+atrazine (37), or compound of formula I+terbuthylazine (775)).

Mixtures of a compound of formula I with an HPPD inhibitor (e.g. compound of formula I+isoxaflutole (479), compound of formula I+mesotrione (515), compound of formula I+pyrasulfotole (CAS RN 365400-11-9), compound of formula I+sulcotrione (747), compound of formula I+tembotrione (CAS RN 335104-84-2), compound of formula I+topramezone (CAS RN 210631-68-8), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), or compound of formula I+4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula I with an HPPD inhibitor and a triazine.

Mixtures of a compound of formula I with glyphosate (419).

Mixtures of a compound of formula I with glyphosate and an HPPD inhibitor (e.g. compound of formula I+glyphosate+isoxaflutole, compound of formula I+glyphosate+mesotrione, compound of formula I+glyphosate+pyrasulfotole (CAS RN 365400-11-9), compound of formula I+glyphosate+sulcotrione, compound of formula I+glyphosate+tembotrione, compound of formula I+glyphosate+topramezone, compound of formula I+glyphosate+4-hydroxy-3-[[2-[(2-methoxyethoxy)methyl]-6-(trifluoromethyl)-3-pyridinyl]carbonyl]-bicyclo[3.2.1]oct-3-en-2-one, or compound of formula I+glyphosate+4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula I with glufosinate-ammonium (418).

Mixtures of a compound of formula I with glufosinate-ammonium and an HPPD inhibitor (e.g. compound of formula I+glufosinate-ammonium+isoxaflutole, compound of formula I+glufosinate-ammonium+mesotrione, compound of formula I+glufosinate-ammonium+pyrasulfotole (CAS RN 365400-11-9), compound of formula I+glufosinate-ammonium+sulcotrione, compound of formula I+glufosinate-ammonium+tembotrione, compound of formula I+glufosinate-ammonium+topramezone, compound of formula I+glufosinate-ammonium+4-hydroxy-3-[[2-[(2-methoxyethoxy)methyl]-6-(trifluoromethyl)-3-pyridinyl]carbonyl]-bicyclo[3.2.1]oct-3-en-2-one, or compound of formula I+glufosinate-ammonium+4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula I with an ALS or an AHAS inhibitor (e.g. compound of formula I+bensulfuron-methyl (64), compound of formula I+chlorimuron-ethyl (135), compound of formula I+cloransulam-methyl (164), compound of formula I+florasulam (359), compound of formula I+flucarbazone-sodium (364), compound of formula I+imazamox (451), compound of formula I+imazapyr (453), compound of formula I+imazethapyr (455), compound of formula I+iodosulfuron-methyl-sodium (466), compound of formula I+mesosulfuron-methyl (514), compound of formula I+nicosulfuron (577), compound of formula I+penoxsulam (622), compound of formula I+pyroxsulam (triflosulam) (CAS RN 422556-08-9), compound of formula I+thifensulfuron-methyl (thiameturon-methyl) (795), compound of formula I+triasulfuron (817), compound of formula I+tribenuron-methyl (822), compound of formula I+trifloxysulfuron-sodium (833), compound of formula I+thiencarbazone (4-[(4,5-dihydro-3-methoxy-4-methyl-5-oxo-1H-1,2,4-triazol-1-yl)carbonylsulfamoyl]-5-methylthiophene-3-carboxylic acid, BAY636)), or compound of formula I+thiencarbazone-methyl (methyl 4-[(4,5-dihydro-3-methoxy-4-methyl-5-oxo-1H-1,2,4-triazol-1-yl)carbonylsulfamoyl]-5-methylthiophene-3-carboxylate, CAS RN 317815-83-1, BAY636-methyl)).

Mixtures of a compound of formula I with a PPO inhibitor (e.g. compound of formula I+butafenacil (101), compound of formula I+carfentrazone-ethyl (121), compound of formula I+cinidon-ethyl (152), compound of formula I+flumioxazin (376), compound of formula I+fomesafen (401), or compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6).

Mixtures of a compound of formula I with an ACCase inhibitor (e.g. compound of formula I+butroxydim (106), compound of formula I+clethodim (155), compound of formula I+clodinafop-propargyl (156), compound of formula I+cycloxydim (190), compound of formula I+cyhalofop-butyl (195), compound of formula I+diclofop-methyl (238), compound of formula I+fenoxaprop-P-ethyl (339), compound of formula I+fluazifop-butyl (361), compound of formula I+fluazifop-P-butyl (362), compound of formula I+haloxyfop (427), compound of formula I+haloxyfop-P (428), compound of formula I+propaquizafop (670), compound of formula I+quizalofop (717), compound of formula I+quizalofop-P (718), compound of formula I+sethoxydim (726), compound of formula I+tepraloxydim (771), compound of formula I+tralkoxydim (811)), or compound of formula I+pinoxaden (CAS RN 243973-20-8).

Mixtures of a compound of formula I with prosulfocarb (683), or a compound of formula I with tri-allate (816).

Mixtures of a compound of formula I with bromoxynil (95), a compound of formula I with chloridazon (134), a compound of formula I with chlorotoluron (143), a compound of formula I with diuron (281), or a compound of formula I with metribuzin (554).

Mixtures of a compound of formula I with clomazone (159), a compound of formula I with diflufenican (251), a compound of formula I with fluorochloridone (389), or a compound of formula I with flurtamone (392).

Mixtures of a compound of formula I with pendimethalin (621) or a compound of formula I with trifluralin (836).

Mixtures of a compound of formula I with difenzoquat metilsulfate (248).

Mixtures of a compound of formula I with diquat dibromide (276).

Mixtures of a compound of formula I with paraquat dichloride (614). The mixing partners of the compound of formula I may also be in the form of esters or salts, as mentioned e.g. in The Pesticide Manual, 13$^{rh 11}$ Edition (BCPC), 2003. The reference to glufosinate-ammonium also applies to glufosinate, the reference to cloransulam-methyl also applies to cloransulam, the reference to dimethenamid also applies to dimethenamid-P, the reference to flamprop-M also applies to flamprop, and the reference to pyrithiobac-sodium also applies to pyrithiobac, etc.

The mixing ratio of the compound of formula I to the mixing partner is preferably from 1:100 to 1000:1.

The mixtures can advantageously be used in the above-mentioned formulations (in which case "active ingredient" relates to the respective mixture of compound of formula I with the mixing partner).

Additionally, one or more of the following herbicides can be used in combination with a compound of formula I according to the invention or in combination with a mixture as described above: acifluorfen-sodium (7), aclonifen (8), acrolein (10), alachlor (14), alloxydim (18), ametryn (20), amicarbazone (21), amidosulfuron (22), amitrole (aminotriazole) (25), ammonium sulfamate (26), anilofos (31), asulam (36), aviglycine (39), azafenidin (CAS RN 68049-83-2), azimsulfuron (43), BAS 800H(CAS RN 372137-35-4), beflubutamid (55), benazolin (57), bencarbazone (CAS RN 173980-17-1), benfluralin (59), benfuresate (61), bensulide (65), bentazone (67), benzfendizone (CAS RN 158755-95-4), benzobicyclon (69), benzofenap (70), bilanafos (bialaphos) (77), bispyribac-sodium (82), borax (86), bromacil (90), bromobutide (93), bromofenoxim (CAS RN 13181-17-4), butachlor (100), butamifos (102), butralin (105), butylate (108), cafenstrole (110), carbetamide (117), chlorbromuron (CAS RN 13360-45-7), chlorflurenol-methyl (133), chloroacetic acid (138), chlorpropham (144), chlorsulfuron (147), chlorthal-dimethyl (148), cinmethylin (153), cinosulfuron (154), clomeprop (160), cumyluron (180), cyanamide (182), cyanazine (183), cyclanilide (186), cycloate (187), cyclosulfamuron (189), daimuron (213), dalapon (214), dazomet (216), desmediphain (225), desmetryn (CAS RN 1014-69-3), dichlobenil (229), dichlorprop (234), dichlorprop-P (235), diclosulam (241), dimefuron (256), dimepiperate (257), dimethachlor (258), dimethametryn (259), dimethipin (261), dimethylarsinic acid (264), dinitramine (268), dinoterb (272), diphenamid (274), dipropetryn (CAS RN 4147-51-7), dithiopyr (280), DNOC (282), DSMA (CAS RN 144-21-8), endothal (295), EPTC (299), esprocarb (303), ethalfluralin (305), ethametsulfuron-methyl (306), ethephon (307), ethofumesate (311), ethoxyfen (CAS RN 188634-90-4), ethoxyfen-ethyl (CAS RN 131086-42-5), ethoxysulfuron (314), etobenzanid (318), fentrazamide (348), ferrous sulfate (353), flazasulfuron (356), fluazolate (isopropazol) (CAS RN 174514-07-9), flucetosulfuron (CAS RN 412928-75-7), fluchloralin (365), flufenpyr-ethyl (371), flumetralin (373), flumetsulam (374), flumiclorac-pentyl (375), flumipropyn (flumipropin) (CAS RN 84478-52-4), fluometuron (378), fluoroglycofen-ethyl (380), flupoxam (CAS RN 119126-15-7), fluropacil (CAS RN 120890-70-2), flupropanate (383), flupyrsulfuron-methyl-sodium (384), flurenol (387), fluridone (388), fluoroxypyr (390), fluthiacet-methyl (395), foramsulfuron (402), fosamine (406), halosulfuron-methyl (426), HC-252 (429), hexazinone (440), imazamethabenz-methyl (450), imazapic (452), imazaquin (454), imazosulfuron (456), indanofan (462), ioxynil (467), isoproturon (475), isouron (476), isoxaben (477), isoxachlortole (CAS RN 141112-06-3), isoxapyrifop (CAS RN 87757-18-4), karbutilate (482), lactofen (486), lenacil (487), linuron (489), MCPA-thioethyl (500), MCPB (501), mecoprop (503), mecoprop-P (504), mefenacet (505), mefluidide (507), metam (519), metamifop (mefluoxafop) (520), metamitron (521), metazachlor (524), methabenzthiazuron (526), methazole (CAS RN 20354-26-1), methylarsonic acid (536), methyldymron (539), methyl isothiocyanate (543), metobenzuron (547), metobromuron (CAS RN 3060-89-7), metosulam (552), metoxuron (553), metsulfuron-methyl (555), MK-616 (559), molinate (560), monolinuron (562), MSMA (CAS RN 2163-80-6), naproanilide (571), napropamide (572), naptalam (573), neburon (574), nipyraclofen (CAS RN 99662-11-0), n-methyl-glyphosate, nonanoic acid (583), norflurazon (584), oleic acid (fatty acids) (593), orbencarb (595), orthosulfamuron (CAS RN 213464-77-8), oryzalin (597), oxadiargyl (599), oxadiazon (600), oxasulfuron (603), oxaziclomefone (604), oxyfluorfen (610), pebulate (617), pentachlorophenol (623), pentanochlor (624), pentoxazone (625), pethoxamid (627), petrolium oils (628), phenmedipham (629), picloram (645), picolinafen (646), piperophos (650), primisulfuron-methyl (657), prodiamine (661), profluazol (CAS RN 190314-43-3), profoxydim (663), prohexadione calcium (664), prometon (665), prometryn (666), propachlor (667), propanil (669), propazine (672), propham (674), propisochlor (667), propoxycarbazone-sodium (procarbazone-sodium) (679), propyzamide (681), prosulfuron (684), pyraclonil (pyrazogyl) (CAS RN 158353-15-2), pyraflufen-ethyl (691), pyrazolynate (692), pyrazosulfuron-ethyl (694), pyrazoxyfen (695), pyribenzoxim (697), pyributicarb (698), pyridafol (CAS RN 40020-01-7), pyridate (702), pyriftalid (704), pyriminobac-methyl (707), pyrimisulfan (CAS RN 221205-90-9), pyrithiobac-sodium (709), quinmerac (713), quinoclamine (714), rimsulfuron (721), sequestrene, siduron (727), simazine (730), simetryn (732), sodium chlorate (734), sulfentrazone (749), sulfometuron-methyl (751), sulfosate (CAS RN 81591-81-3), sulfosulfuron (752), sulfuric acid (755), tar oils (758), TCA-sodium (760), tebutam (CAS RN 35256-85-0), tebuthiuron (765), tefuryltrione (CAS RN 473278-76-1), terbacil (772), terbumeton (774), terbutryn (776), thenylchlor (789), thidiazimin (CAS RN 123249-43-4), thiazafluoron (CAS RN 25366-23-8), thiazopyr (793), thiobencarb (797), tiocarbazil (807), triaziflam (819), triclopyr (827), trietazine (831), triflusulfuron-methyl (837), trihydroxytriazine (CAS RN 108-80-5), trinexapac-ethyl (CAS RN 95266-40-3) and tritosulfuron (843).

The mixing partners of the compound of formula I may also be in the form of esters or salts, as mentioned e.g. in The Pesticide Manual, 13$^{th}$ Edition (BCPC), 2003. The reference to acifluorfen-sodium also applies to acifluorfen, and the reference to bensulfuron-methyl also applies to bensulfuron, etc.

The mixing ratio of the compound of formula I to the mixing partner is preferably from 1:100 to 1000:1.

The mixtures can advantageously be used in the above-mentioned formulations (in which case "active ingredient" relates to the respective mixture of compound of formula I with the mixing partner).

The compounds of formula I according to the invention can also be used in combination with one or more safeners. Likewise, mixtures of a compound of formula I according to the invention with one or more further herbicides can also be used in combination with one or more safeners. The safeners can be benoxacor (63), cloquintocet-mexyl (163), cyometrinil (CAS RN 78370-21-5), cyprosulfamide (CAS RN 221667-31-8), dichlormid (231), dicyclonon (CAS RN 79260-71-2), fenchlorazole-ethyl (331), fenclorim (332), flurazole (386), fluxofenim (399), furilazole (413) and the corresponding R isomer, isoxadifen-ethyl (478), mefenpyr-diethyl (506), naphthalic anhydride (CAS RN 81-84-5), and oxabetrinil (598). Particularly preferred are mixtures of a compound of formula I with benoxacor and a compound of formula I with cloquintocet-mexyl.

The safeners of the compound of formula I may also be in the form of esters or salts, as mentioned e.g. in The Pesticide Manual, 13$^{th}$ Edition (BCPC), 2003. The reference to cloquintocet-mexyl also applies to cloquintocet, and the reference to fenchlorazole-ethyl also applies to fenchlorazole, etc.

Preferably the mixing ratio of compound of formula I to safener is from 100:1 to 1:10, especially from 20:1 to 1:1.

The mixtures can advantageously be used in the above-mentioned formulations (in which case "active ingredient" relates to the respective mixture of compound of formula I with the safener). It is possible that the safener and a compound of formula I and one or more additional herbicide(s), if any, are applied simultaneously. For example, the safener, a compound of formula I and one or more additional herbicide(s), if any, might be applied to the locus pre-emergence or might be applied to the crop post-emergence. It is also possible that the safener and a compound of formula I and one or more additional herbicide(s), if any, are applied sequentially. For example, the safener might be applied before sowing the seeds as a seed treatment and a compound of formula I and one or more additional herbicides, if any, might be applied to the locus pre-emergence or might be applied to the crop post-emergence.

Preferred mixtures of a compound of formula I with further herbicides and safeners include:

Mixtures of a compound of formula I with a triazine and a safener.

Mixtures of a compound of formula I with glyphosate and a safener.

Mixtures of a compound of formula I with glufosinate and a safener.

Mixtures of a compound of formula I with isoxaflutole and a safener.

Mixtures of a compound of formula I with isoxaflutole and a triazine and a safener.

Mixtures of a compound of formula I with isoxaflutole and glyphosate and a safener.

Mixtures of a compound of formula I with isoxaflutole and glufosinate and a safener.

Mixtures of a compound of formula I with mesotrione and a safener.

Mixtures of a compound of formula I with mesotrione and a triazine and a safener.

Mixtures of a compound of formula I with mesotrione and glyphosate and a safener.

Mixtures of a compound of formula I with mesotrione and glufosinate and a safener.

Mixtures of a compound of formula I with sulcotrione and a safener.

Mixtures of a compound of formula I with sulcotrione and a triazine and a safener.

Mixtures of a compound of formula I with sulcotrione and glyphosate and a safener.

Mixtures of a compound of formula I with sulcotrione and glufosinate and a safener.

The following Examples further illustrate, but do not limit, the invention.

PREPARATION EXAMPLES

1. Reactions which are Covered by Scheme 1

Example 1.1

Preparation of 3-[2-(2-chloro-3,6-difluoro-phenyl)-acetylamino]-pyrazine-2-carboxylic acid methyl ester

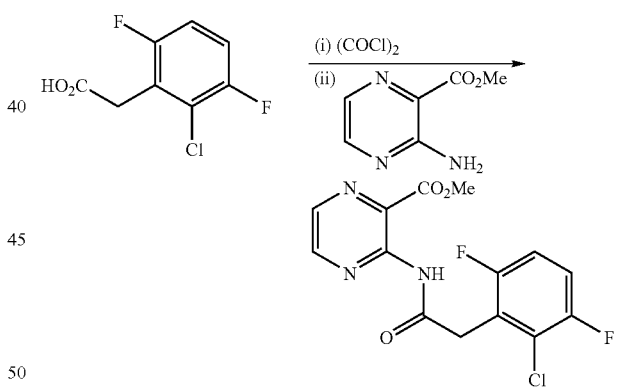

Oxalyl chloride (1.30 ml) was added dropwise to a solution of (2-chloro-3,6-difluoro-phenyl)-acetic acid (3.151 g) in dichloromethane (20 ml) and a drop of N,N-dimethylformamide was added to initiate the reaction. The reaction mixture was stirred at ambient temperature for 1 hour. The solvent was evaporated to produce a colourless oil which was dissolved in acetonitrile (30 ml). This solution was then divided into three portions and each portion was added to a slurry of 3-amino-pyrazine-2-carboxylic acid methyl ester (0.76 g) in acetonitrile (15 ml). The reaction mixtures were heated in the microwave at 130° C. for 40 minutes to produce dark red solutions that was stored at ambient temperature for 16 hours. The samples were combined and concentrated to produce 3-[2-(2-chloro-3,6-difluoro-phenyl)-acetylamino]-pyrazine-2-carboxylic acid methyl ester as a dark orange solid (4.15 g).

¹H-NMR (400 MHz, CDCl₃): 4.02 (s, 3H), 4.22 (s, 2H), 7.02-7.10 (m, 1H), 7.11-7.17 (m, 1H), 8.41 (d, 1H), 8.61 (d, 1H), 10.8 (s, 1H) ppm.

Example 1.2

Preparation of 7-(2-chloro-3,6-difluoro-phenyl)-8-hydroxy-5H-pyrido[2,3-b]pyrazin-6-one

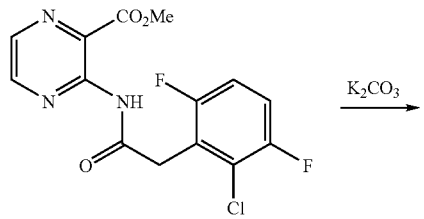

3-[2-(2-Chloro-3,6-difluoro-phenyl)-acetylamino]-pyrazine-2-carboxylic acid methyl ester (4.15 g) (Example 1.1) was heated with potassium carbonate (1.67 g) in N,N-dimethylformamide (50 ml) at 110° C. for 2 hours and then stored at ambient temperature for 16 hours. Water was added and the reaction mixture was acidified with aqueous hydrochloric acid (concentrated). A precipitate formed which was isolated by filtration. The residue was washed successively with water and hexane to produce 7-(2-chloro-3,6-difluoro-phenyl)-8-hydroxy-5H-pyrido[2,3-b]pyrazin-6-one as a brown solid (2.88 g). ¹H-NMR (400 MHz, d₆-DMSO): 7.34-7.42 (m, 1H), 7.51-7.59 (m, 1H), 8.59 (d, 1H), 8.72 (d, 1H), 12.0 (bs, 1H), 12.4 (s, 1H) ppm.

Example 1.3

Preparation of 2,2-dimethyl-propionic acid 7-(2-chloro-3,6-difluoro-phenyl)-6-oxo-5,6-dihydro-pyrido[2,3-b]pyrazin-8-yl ester

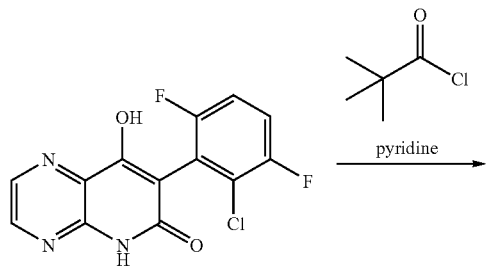

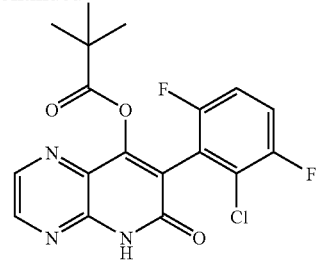

A mixture of 7-(2-chloro-3,6-difluoro-phenyl)-8-hydroxy-5H-pyrido[2,3-b]pyrazin-6-one (0.20 g) (Example 1.2), trimethylacetyl chloride (0.08 ml), and pyridine (0.05 ml) in dichloromethane (5 ml) was stirred at ambient temperature for two hours. The reaction mixture was diluted with ethyl acetate and water. The phases were separated. The organic phase was dried over magnesium sulfate and concentrated to produce a yellow semi-crystalline oil. This was triturated in iso-hexane to produce 2,2-dimethyl-propionic acid 7-(2-chloro-3,6-difluoro-phenyl)-6-oxo-5,6-dihydro-pyrido[2,3-b]pyrazin-8-yl ester as a pale brown powder (0.113 g). ¹H-NMR (400 MHz, CDCl₃): 1.21 (s, 9H), 7.08-7.13 (m, 1H), 7.21-7.27 (m, 1H), 8.55-8.57 (m, 2H), 9.51 (s, 1H) ppm.

2. Reactions which are Covered by Scheme 2

Example 2.1

Preparation of 2,2-dimethyl-propionic acid 7-(2-chloro-3,6-difluoro-phenyl)-5-(2,2-difluoro-ethyl)-6-oxo-5,6-dihydro-pyrido[2,3-b]pyrazin-8-yl ester (Compound No. A2 of Table A)

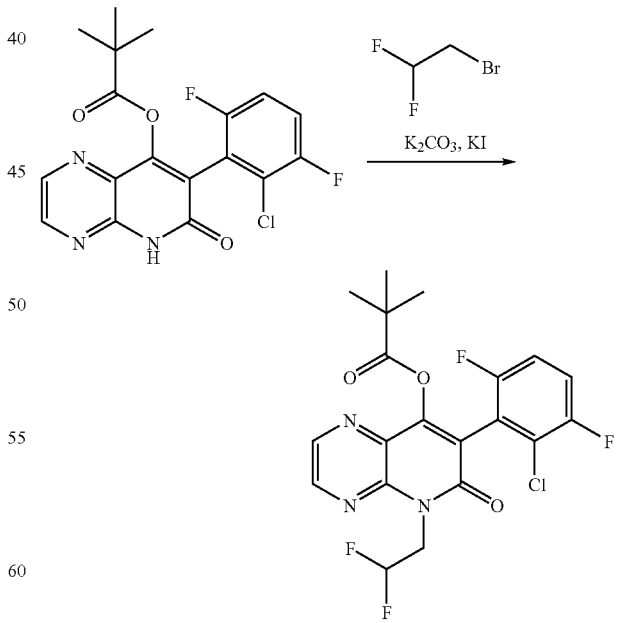

1-Bromo-2,2-difluoroethane (0.113 g) was added to a mixture of 2,2-dimethyl-propionic acid 7-(2-chloro-3,6-difluorophenyl)-6-oxo-5,6-dihydro-pyrido[2,3-b]pyrazin-8-yl ester (Example 1.3) (0.126 g), potassium carbonate (0.044 g) and potassium iodide (0.053 g) in acetonitrile (5 ml). The reaction mixture was heated in a microwave for 25 minutes at 120° C. The reaction mixture was concentrated and the residue was purified by column chromatography on silica gel (eluent: hexane/ethyl acetate, 8:2 to 1:1) to give Compound No. A2 of Table A as a yellow solid (0.083 g).

Example 2.2

Preparation of 2,2-dimethyl-propionic acid 7-(2-chloro-3,6-difluoro-phenyl)-5-(2-fluoro-ethyl)-6-oxo-5,6-dihydro-pyrido[2,3-b]pyrazin-8-yl ester (Compound No. C9 of Table C)

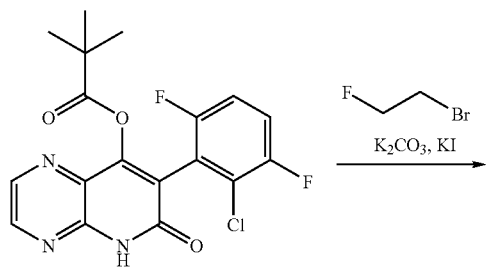

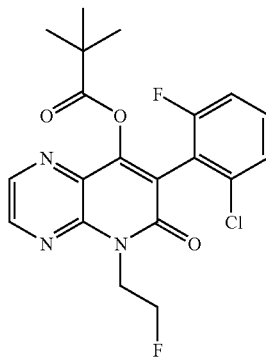

2-Fluoroethyl bromide was added to a mixture of 2,2-dimethyl-propionic acid 7-(2-chloro-3,6-difluoro-phenyl)-6-oxo-5,6-dihydro-pyrido[2,3-b]pyrazin-8-yl ester (Example 1.3) (0.20 g), potassium carbonate (0.207 g) and potassium iodide (catalytic amount) in N,N-dimethylformamide (10 ml). The reaction mixture was heated in the microwave for 20 minutes at 120° C. The reaction mixture was concentrated and the residue was purified by column chromatography on silica gel (eluent: ethyl acetate/hexane 1:1) to give Compound No. C9 of Table C as a yellow solid (0.103 g).

Example 2.3

Preparation of 2,2-dimethyl-propionic acid 7-(2-chloro-3,6-difluoro-phenyl)-5-(2,2,2-trifluoro-ethyl)-6-oxo-5,6-dihydro-pyrido[2,3-b]pyrazin-8-yl ester (Compound No. C8 of Table C)

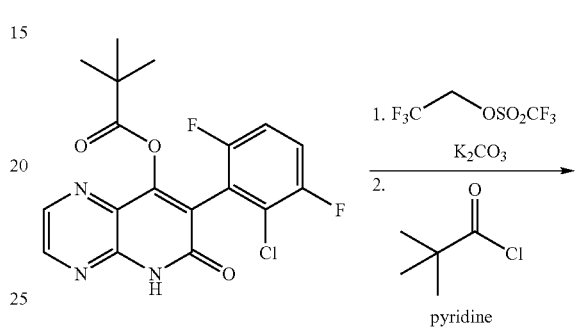

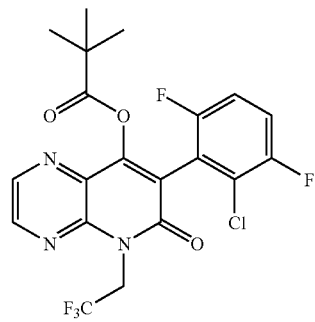

A mixture of 2,2-dimethyl-propionic acid 7-(2-chloro-3,6-difluoro-phenyl)-6-oxo-5,6-dihydro-pyrido[2,3-b]pyrazin-8-yl ester (is this correct or did the reaction start with the unprotected species?) (Example 1.3) (0.10 g), potassium carbonate (0.053 g) and 2,2,2-trifluoroethyl triflate (0.130 g) were heated in a microwave at 150° C. for 30 minutes, and then at 170° C. for 30 minutes. The reaction mixture was allowed to cool to ambient temperature and was then partitioned between dichloromethane and aqueous hydrochloric acid (2M). The phases were separated. The organic layer was dried over magnesium sulfate and concentrated. The residue was dissolved in dichloromethane and treated with trimethylacetyl chloride (0.063 ml) and pyridine (0.061 ml) and stirred at ambient temperature. The reaction mixture was concentrated and the residue was purified by column chromatography on silica gel (eluent: acetone/iso-hexane 0:10 to 1:9) to give Compound No. C8 of Table C as a beige solid (0.049 g).

Example 2.4

Preparation of 7-(2-chloro-3,6-difluoro-phenyl)-5-(2,2-difluoro-ethyl)-8-hydroxy-5H-pyrido[2,3-b]pyrazin-6-one (Compound No. B2 of Table B)

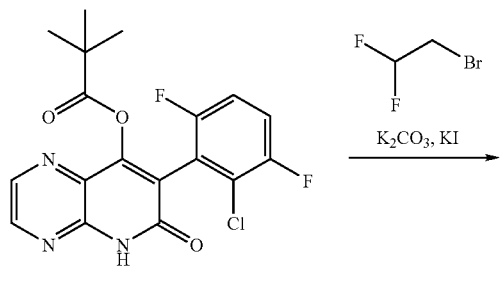

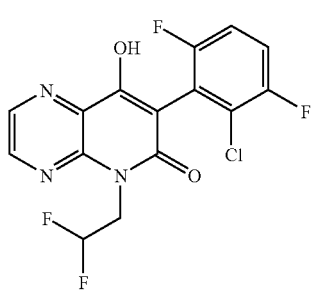

1-Bromo-2,2-difluoroethane (0.754 g) was added to a mixture of 2,2-dimethyl-propionic acid 7-(2-chloro-3,6-difluoro-phenyl)-6-oxo-5,6-dihydro-pyrido[2,3-1)]pyrazin-8-yl ester (Example 1.3) (1.00 g), potassium carbonate (1.76 g) and potassium iodide (catalytic amount) in anhydrous N,N-dimethylformamide (15 ml). The reaction mixture was heated in a microwave for 20 minutes at 120° C. The reaction mixture was allowed to cool to ambient temperature before diluting with water and ethyl acetate. The phases were separated. The organic phase was washed with water, dried over magnesium sulfate, and concentrated. The residue was dissolved in diethyl ether, and the solution was washed with water. The phases were separated and the organic phase was concentrated to give Compound No. B2 of Table B as an orange viscous oil (0.553 g).

The compounds mentioned in Tables A to D below can be prepared using analogous methods to those described in Example 2.1, 2.2., 2.3 and 2.4.

3. Reactions which are Covered by Scheme 3

Example 3.1

Preparation of 3-[2-(2,3,6-trichloro-phenyl)-acetylamino]-pyrazine-2-carboxylic acid

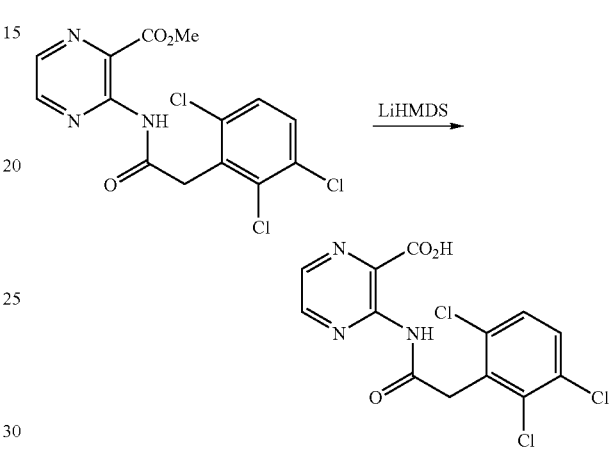

Lithium hexamethyldisilazide ("LiHMDS") (1M in THF) (2 ml) was added dropwise to a solution of 3-[2-(2,3,6-trichloro-phenyl)-acetylamino]-pyrazine-2-carboxylic acid methyl ester (0.373 g) (which was made as described in Example 1.1) in anhydrous tetrahydtofuran (10 ml). The reaction mixture was stirred for 30 minutes at ambient temperature and then heated to reflux for three hours. The reaction mixture was allowed to cool to ambient temperature and acidified by addition of aqueous hydrochloric acid (1M). The mixture was concentrated. The residue was dissolved in diethyl ether and washed with aqueous hydrochloric acid (1M). The acid solution was extracted with ethyl acetate. The combined organic fractions were dried over magnesium sulfate and concentrated to give 3-[2-(2,3,6-trichloro-phenyl)-acetylamino]-pyrazine-2-carboxylic acid (0.225 g) which was carried on to the next step without further purification.

Example 3.2

Alternative preparation of 5-(2,2-difluoro-ethyl)-8-hydroxy-7-(2,3,6-trichloro-phenyl)-5H-pyrido[2,3-b]pyrazin-6-one (Compound No. B11 of Table B)

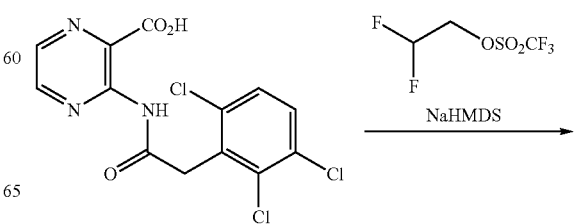

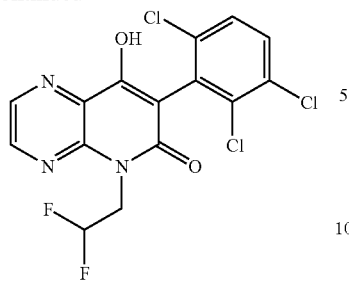

Sodium hexamethyldisilazide ("NaHMDS") (1M in THF) (1.4 ml) was added dropwise to a solution of 3-[2-(2,3,6-trichloro-phenyl)-acetylamino]-pyrazine-2-carboxylic acid (Example 3.1) (0.225 g) in anhydrous tetrahydrofuran (10 ml) over a period of 10 minutes. Then difluoroethyl triflate (0.270 g) was added dropwise and the reaction mixture was allowed to stir at ambient temperature for 30 minutes. Then the reaction mixture was heated to reflux for 6 hours. The reaction mixture was allowed to cool to ambient temperature and acidified by addition of aqueous hydrochloric acid (1M). The mixture was concentrated. The residue was dissolved in diethyl ether and washed with aqueous hydrochloric acid (1M). The acid solution was extracted with ethyl acetate. The combined organic fractions were dried over magnesium sulfate and concentrated. The residue was purified by reverse phase HPLC to give Compound No. B11 of Table B (0.034 g).

4. Reactions which are Covered by Scheme 10

Example 4.1

Preparation of
1-bromo-3-bromomethyl-2-chloro-4-fluoro-benzene

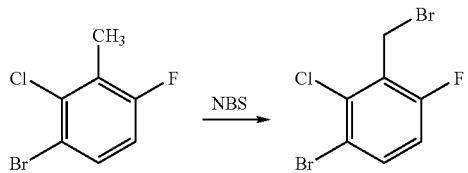

A mixture of 3-bromo-2-chloro-6-fluoro-toluene (8.0 g), N-bromosuccinimide ("NBS") (6.42 g) and benzoyl peroxide (catalytic amount) in carbon tetrachloride (40 ml) was heated to reflux. A 500 watt tungsten halogen lamp was used to initiate the reaction. The reaction mixture was heated to reflux and irradiated for 30 minutes. The reaction mixture was allowed to cool to ambient temperature and then filtered. The filtrate was concentrated to give a colourless oil which solidified on standing to give 1-bromo-3-bromomethyl-2-chloro-4-fluoro-benzene as an off-white solid (10.7 g). $^1$H-NMR (400 MHz, CDCl$_3$): 4.64 (d, 2H), 6.94 (t, 1H), 7.58 (dd, 1H) ppm.

Example 4.2

Preparation of
(3-bromo-2-chloro-6-fluoro-phenyl)-acetonitrile

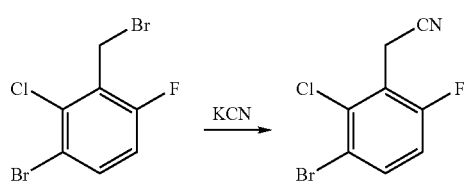

A solution of 1-bromo-3-bromomethyl-2-chloro-4-fluoro-benzene (9.945 g) (Example 4.2) in absolute ethanol (40 ml) was added dropwise to a solution of potassium cyanide (2.38 g) in water (2 ml) under heating over a period of 30 minutes. The reaction mixture was heated to reflux for 7 hours. The reaction mixture was then allowed to cool to ambient temperature and then stored at ambient temperature for 16 hours. The mixture was filtered and the filtrate concentrated. The residue was dissolved in ethyl acetate, dried over magnesium sulfate and concentrated to give (3-bromo-2-chloro-6-fluoro-phenyl)-acetonitrile as a pale yellow oil (8.19 g). $^1$H-NMR (400 MHz, CDCl$_3$): 3.89 (d, 2H), 7.00 (t, 1H), 7.64 (dd, 1H) ppm.

Example 4.3

Preparation of
(3-bromo-2-chloro-6-fluoro-phenyl)-acetic acid

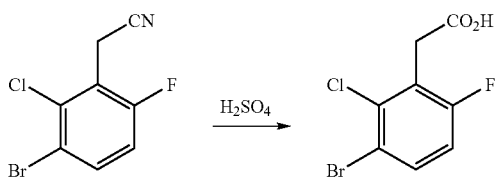

(3-Bromo-2-chloro-6-fluoro-phenyl)-acetonitrile (8.15 g) (Example 4.3) was dissolved in concentrated sulfuric acid (50% by weight in water) (90 ml). The reaction became very hot and was then heated to reflux for 3 hours. The reaction mixture was allowed to cool to ambient temperature and was stored at ambient temperature for 16 hours. The mixture was extracted twice with dichloromethane. The combined organic phases were dried over magnesium sulfate and concentrated to give (3-bromo-2-chloro-6-fluoro-phenyl)-acetic acid as an off-white solid (8.3 g). $^1$H-NMR (400 MHz, CDCl$_3$): 3.94 (d, 2H), 6.94 (t, 1H), 7.56 (dd, 1H) ppm.

5. Reactions which are Covered by Scheme 12

Example 5.1

Preparation of 3-amino-6-methyl-pyrazine-2-carboxylic acid methyl ester

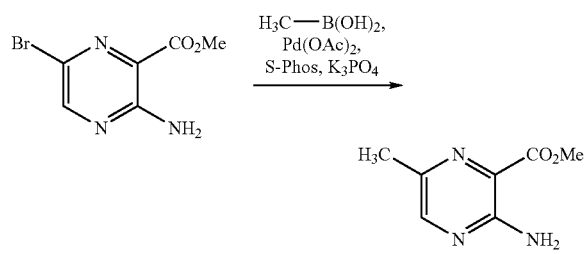

3-Amino-6-bromo-pyrazine-2-carboxylic acid methyl ester (1.0 g) (made according to J. Org. Chem. (1988), 59(9), 2052-5), palladium(II) acetate (0.101 g), and 2'-dicyclohexylphosphino-2,6-dimethoxy-1,1'-biphenyl ("S-Phos") were placed in a flask with toluene (15 ml) and water (3 drops). Methyl boronic acid (0.394 g) and potassium phosphate (1.71 g) were added and the reaction mixture was heated to reflux for 24 hours. After allowing the reaction mixture to cool to ambient temperature, the mixture was diluted with aqueous hydrochloric acid (1M) and extracted with ethyl acetate. The combined organic extracts were concentrated and the residue was purified by column chromatography on silica gel (eluent: diethyl ether) to give 3-amino-6-methyl-pyrazine-2-carboxylic acid methyl ester as a yellow solid (0.114 g). $^1$H-NMR (400 MHz, CDCl$_3$): 2.40 (s, 3H), 3.92 (s, 3H), 6.21 (bs, 2H), 8.03 (s, 1H) ppm.

TABLE A

Compounds of formula (Ia"), i.e. compounds of formula (I) wherein $R^3$ is 2,2-difluoro-ethyl, and $R^1$, $R^2$, $R^4$ and $R^5$ have the values as defined in the table below.

(Ia")

| Compound No | $R^1$ | $R^2$ | $R^4$ | $R^5$ | $^1$H-NMR (400 MHz, CDCl$_3$ unless indicated otherwise) |
|---|---|---|---|---|---|
| A1 | H | H | 2-F$_3$CO-phenyl- | t-Bu—(CO)O— | 1.19 (s, 9H), 4.98 (dt, 2H), 6.25 (tt, 1H), 7.33-7.40 (m, 3H), 7.47-7.51 (m, 1H), 8.54 (d, 1H), 8.59 (d, 1H). |
| A2 | H | H | 2-Cl-3,6-di-F-phenyl- | t-Bu—(CO)O— | 1.21 (s, 9H), 4.98 (dt, 2H), 6.27 (tt, 1H), 7.07-7.13 (m, 1H), 7.21-7.27 (m, 1H), 8.57 (d, 1H), 8.62 (d, 1H). |
| A3 | H | H | 2-Cl-3,6-di-F-phenyl- | i-Pr—(CO)O— | 1.17 (dd, 6H), 2.81 (sept, 1H), 4.98 (dt, 2H), 6.26 (tt, 1H), 7.08-7.14 (m, 1H), 7.21-7.28 (m, 1H), 8.58 (d, 1H), 8.63 (d, 1H). |
| A4 | H | H | 2-Cl-3-F$_3$C-phenyl- | i-Pr—(CO)O— | 1.10 (d, 6H), 2.72 (d, 3H), 5.02 (m, 1H), 6.01-6.40 (tt, 1H), 7.37 (m, 1H), 7.60 (m, 1H), 8.58 (d, 1H), 8.62 (d, 1H). |
| A5 | H | H | 2-Cl-6-F-5-Me-phenyl- | t-Bu—(CO)O— | 1.17 (s, 9H), 2.27 (d, 3H), 3.87 (s, 3H), 7.19 (m, 2H), 8.49 (d, 1H), 8.58 (d, 1H). |
| A6 | H | H | 2-Cl-6-F-5-Me-phenyl- | i-Pr—(CO)O— | 1.10 (d, 3H), 1.11 (d, 3H), 2.27 (d, 3H), 2.77 (sept, 1H), 3.86 (s, 3H), 7.19 (d, 2H), 8.49 (d, 1H), 8.59 (d, 1H). |
| A7 | H | H | 2-Cl-5-F$_3$C-phenyl- | i-Pr—(CO)O— | 1.07 (d, 3H), 1.14 (d, 3H), 2.76 (sept, 1H), 4.97 (dt, 2H), 6.25 (tt, 1H), 7.56 (s, 1H), 7.65 (d, 2H), 8.56 (d, 1H), 8.61 (d, 1H). |

TABLE A-continued

Compounds of formula (Ia"), i.e. compounds of formula (I) wherein R³ is 2,2-difluoro-ethyl, and R¹, R², R⁴ and R⁵ have the values as defined in the table below.

(Ia")

| Compound No | R¹ | R² | R⁴ | R⁵ | ¹H-NMR (400 MHz, CDCl₃ unless indicated otherwise) |
|---|---|---|---|---|---|
| A8 | H | H | 2-Cl-5-F₃C-phenyl- | t-Bu—(CO)O— | 1.16 (s, 9H), 4.97 (dt, 2H), 6.25 (tt, 1H), 7.56 (s, 1H), 7.64 (m, 2H), 8.56 (d, 1H), 8.61 (d, 1H). |
| A9 | H | H | 2,6-di-Cl-4-F₃C-phenyl | t-Bu—(CO)O— | 1.12 (s, 9H), 4.98 (m, 2H), 6.20 (tt, 1H), 7.68 (s, 2H), 8.55 (d, 1H), 8.60 (d, 1H). |
| A10 | H | H | 2-Br-4-F₃C-phenyl- | t-Bu—(CO)O— | 1.16 (s, 9H), 4.94-5.02 (dt, 2H), 6.11-6.42 (tt, 1H), 7.40-7.42 (d, 1H), 7.65-7.67 (dd, 1H), 7.97 (d, 1H), 8.48-8.49 (d, 1H), 8.51-8.52 (d, 1H). |
| A11 | H | H | 2,6-di-Cl-4-F₃CO-phenyl- | t-Bu—(CO)O— | 1.20 (s, 9H), 4.96 (m, 2H), 6.22 (tt, 1H), 7.31 (m, 1H), 7.48 (d, 1H), 8.55 (d, 1H), 8.60 (d, 1H). |
| A12 | H | H | 2,6-di-Et-4-Me-phenyl- | i-Pr—(CO)O— | 1.00 (d, 6H), 1.10 (t, 6H), 2.34-2.42 (m, 4H), 2.36 (s, 3H), 2.63-2.73 (m, 1H), 4.98 (dt, 2H), 6.25 (tt, 1H), 6.99 (s, 2H), 8.52 (d, 1H), 8.57 (d, 1H). |
| A13 | H | H | 2-Cl-5-F-phenyl- | i-Pr—(CO)O— | 1.1 (d, 3H), 1.16 (d, 3H), 2.79 (sept, 1H), 4.57 (dt, 2H), 6.25 (tt, 1H), 7.03 (dd, 1H), 7.11 (m, 1H), 7.46 (dd, 1H), 8.55 (d, 1H), 8.60 (d, 1H). |
| A14 | H | H | 2-Cl-5-F-phenyl- | t-Bu—(CO)O— | 1.18 (s, 9H), 4.96 (dt, 2H), 6.25 (tt, 1H), 7.03 (dd, 1H), 7.10 (m, 1H), 7.47 (dd, 1H), 8.55 (d, 1H), 8.59 (d, 1H). |
| A15 | H | H | 2,3-di-MeO-phenyl- | i-Pr—(CO)O— | 1.09 (d, 3H), 1.14 (d, 3H), 2.75 (sept, 1H), 3.79 (s, 3H), 3.89 (s, 3H), 4.95 (m, 2H), 6.25 (tt, 1H), 6.78 (d, 1H), 6.99 (dd, 1H), 7.09 (t, 1H), 8.50 (d, 1H), 8.54 (d, 1H). |
| A16 | H | H | 2,3-di-MeO-phenyl- | t-Bu—(CO)O— | 1.16 (s, 9H), 3.78 (s, 3H), 3.88 (s, 3H), 4.95 (m, 2H), 6.25 (tt, 1H), 6.77 (d, 1H), 6.98 (dd, 1H), 7.08 (t, 1H), 8.50 (d, 1H), 8.53 (d, 1H). |
| A17 | H | H | 2,4-di-Cl-5-F-phenyl- | t-Bu—(CO)O— | 1.22 (s, 9H), 4.95 (dt, 2H), 6.24 (tt, 1H), 7.12 (d, 1H), 7.58 (d, 1H), 8.56 (d, 1H), 8.60 (d, 1H). |
| A19 | H | H | 3-Br-2-Cl-6-F-phenyl- | t-Bu—(CO)O— | 1.19 (s, 9H), 4.97 (dt, 2H), 6.24 (tt, 1H), 7.02 (t, 1H), 7.70 (d, 1H), 8.56 (d, 1H), 8.60 (d, 1H). |
| A20 | H | H | 2,4-di-Cl-5-F-phenyl- | i-Pr—(CO)O— | 1.15 (d, 3H), 1.20 (d, 3H), 2.81 (sept, 1H), 4.95 (dt, 2H), 6.24 (tt, 1H), 7.11 (d, |

TABLE A-continued

Compounds of formula (Ia″), i.e. compounds of formula (I) wherein $R^3$ is 2,2-difluoro-ethyl, and $R^1$, $R^2$, $R^4$ and $R^5$ have the values as defined in the table below.

(Ia″)

| Compound No | $R^1$ | $R^2$ | $R^4$ | $R^5$ | $^1$H-NMR (400 MHz, CDCl$_3$ unless indicated otherwise) |
|---|---|---|---|---|---|
| A21 | H | H | 3-Br-2-Cl-6-F-phenyl- | i-Pr—(CO)O— | 1H), 7.58 (d, 1H), 8.56 (d, 1H), 8.61 (d, 1H). 1.14 (d, 3H), 1.15 (d, 3H), 2.79 (sept, 1H), 4.96 (dt, 2H), 6.24 (tt, 1H), 7.02 (t, 1H), 7.70 (dd, 1H), 8.56 (d, 1H), 8.61 (d, 1H). |
| A22 | H | H | 2,4,6-tri-Me-phenyl- | i-Pr—(CO)O— | 1.00 (d, 6H), 2.07 (s, 6H), 2.29 (s, 3H), 2.68 (sept, 1H), 4.97 (dt, 2H), 6.25 (tt, 1H), 6.91 (s, 2H), 8.53 (d, 1H), 8.57 (d, 1H). |
| A23 | H | H | 2-MeO-5-F$_3$CO-phenyl- | i-Pr—(CO)O— | 1.10 (d, 3H), 1.15 (d, 3H), 2.76 (sept, 1H), 3.83 (s, 3H), 4.95 (m, 2H), 6.25 (tt, 1H), 7.06 (d, 1H), 7.48 (s, 1H), 7.67 (dd, 1H), 8.52 (d, 1H), 8.57 (d, 1H). |
| A25 | H | H | 2,4,6-tri-Me-phenyl- | t-Bu—(CO)O— | 1.07 (s, 9H), 2.08 (s, 6H), 2.28 (s, 3H), 4.98 (dt, 2H), 6.26 (tt, 1H), 6.91 (s, 2H), 8.52 (d, 1H), 8.55 (d, 1H). |
| A26 | H | H | 2-F$_2$HCO-phenyl- | i-Pr—(CO)O— | 1.13 (d, 3H), 1.17 (d, 3H), 2.78 (sept, 1H), 4.95 (m, 2H), 6.23 (tt, 1H), 6.46 (dd, 1H), 7.29 (m, 3H), 7.46 (m, 1H), 8.53 (d, 1H), 8.57 (d, 1H). |
| A27 | H | H | 2-MeO-5-F$_3$CO-phenyl- | t-Bu—(CO)O— | 1.17 (s, 9H), 3.83 (s, 3H), 4.95 (m, 2H), 6.25 (tt, 1H), 7.05 (d, 1H), 7.48 (s, 1H), 7.67 (dd, 1H), 8.52 (d, 1H), 8.56 (d, 1H). |
| A28 | H | H | 2-F$_2$HCO-phenyl- | t-Bu—(CO)O— | 1.19 (s, 9H), 4.95 (m, 2H), 6.23 (tt, 1H), 6.46 (dd, 1H), 7.29 (m, 3H), 7.45 (m, 1H), 8.53 (d, 1H), 8.57 (d, 1H). |
| A29 | -Me | H | 2-Cl-3,6-di-F-phenyl- | t-Bu—(CO)O— | 1.25 (s, 9H), 2.65 (s, 3H), 4.90-4.50 (m, 2H), 6.10-6.40 (m, 1H), 7.10 (m, 1H), 7.25 (m, 1H), 8.50 (s, 1H). |
| A30 | H | -Me | 2-Cl-3,6-di-F-phenyl- | t-Bu—(CO)O— | 1.20 (s, 9H), 2.70 (s, 3H), 5.00 (m, 2H), 6.10-6.40 (m, 1H), 7.10 (m, 1H), 7.25 (m, 1H), 8.40 (s, 1H). |
| A31 | -Ph | H | 2-Cl-3,6-di-F-phenyl- | t-Bu—(CO)O— | 1.25 (s, 9H), 5.00 (m, 2H), 6.15-6.40 (m, 1H), 7.10 (m, 1H), 7.25 (m, 1H), 7.50 (m, 3H), 8.00 (d, 2H), 9.05 (s, 1H). |
| A32 | H | H | 2,3-di-Cl-6-F-phenyl- | t-Bu—(CO)O— | 1.18 (s, 9H), 4.92-5.02 (m, 2H), 6.25 (tt, 1H), 7.08 (t, 1H), 7.55 (dd, 1H), 8.55 (d, 1H), 8.62 (d, 1H). |
| A33 | H | H | 2-Cl-4,5-di-F- | t-Bu—(CO)O— | 1.22 (s, 9H), 2.95 (m, 2H), 6.35 (tt, 1H), 7.15 (dd, |

TABLE A-continued

Compounds of formula (Ia″), i.e. compounds of formula (I) wherein R³ is 2,2-difluoro-ethyl, and R¹, R², R⁴ and R⁵ have the values as defined in the table below.

(Ia″)

| Compound No | R¹ | R² | R⁴ | R⁵ | ¹H-NMR (400 MHz, CDCl₃ unless indicated otherwise) |
|---|---|---|---|---|---|
| | | | phenyl- | | 1H), 7.30 (dd, 1H), 8.55 (d, 1H), 8.62 (d, 1H). |
| A34 | H | H | 2-Cl-6-F-phenyl- | t-Bu—(CO)O— | 1.20 (s, 9H), 5.01 (m, 2H), 6.35 (tt, 1H), 7.04 (m, 1H), 7.32-7.41 (m, 2H), 8.53 (d, 1H), 8.60 (d, 1H). |
| A35 | H | -Me | 2,6-di-Cl-4-F₃C-phenyl- | t-Bu—(CO)O— | 1.18 (s, 9H), 2.71 (s, 3H), 5.00 (m, 2H), 6.15-6.37 (m, 1H), 7.10 (m, 1H), 7.68 (s, 2H), 8.45 (s, 1H). |
| A36 | H | H | 2-I-phenyl- | t-Bu—(CO)O— | 1.15 (s, 9H), 5.02 (m, 2H), 6.37 (tt, 1H), 7.08 (ddd, 1H), 7.20 (dd, 1H), 7.41 (ddd, 1H), 7.96 (dd, 1H), 8.52 (d, 1H), 8.60 (d, 1H). |
| A37 | H | H | 5-Cl-2-F₃C-phenyl- | t-Bu—(CO)O— | 1.12 (s, 9H), 4.94 (m, 2H), 6.22 (tt, 1H), 7.30 (s, 1H), 7.53 (d, 1H), 7.73 (d, 1H), 8.55 (d, 1H), 8.60 (d, 1H). |
| A38 | H | H | 5-Br-2-MeO-phenyl- | t-Bu—(CO)O— | 1.21 (s, 9H), 3.76 (s, 3H), 4.94 (m, 2H), 6.24 (tt, 1H), 6.87 (d, 1H), 7.31 (s, 1H), 7.49 (dd, 1H), 8.51 (d, 1H), 8.54 (d, 1H). |
| A41 | H | H | 2-Cl-6-F₃C-phenyl- | i-Pr—(CO)O— | 1.03 (d, 3H), 1.08 (d, 3H), 2.72 (sept, 1H), 4.96 (m, 2H), 6.22 (tt, 1H), 7.52 (t, 1H), 7.71 (d, 2H), 8.55 (d, 1H), 8.60 (d, 1H). |
| A42 | H | H | 2,5-di-Cl-phenyl- | t-Bu—(CO)O— | 1.19 (s, 9H), 4.96 (dt, 2H), 6.25 (tt, 1H), 7.28 (d, 1H), 7.35 (dd, 1H), 7.44 (d, 1H), 8.56 (d, 1H), 8.59 (d, 1H). |
| A43 | H | H | 2,5-di-F₃C-phenyl- | t-Bu—(CO)O— | 1.08 (s, 9H), 4.95 (m, 2H), 6.22 (tt, 1H), 7.58 (s, 1H), 7.84 (d, 1H), 7.94 (d, 1H), 8.56 (d, 1H), 8.61 (d, 1H). |
| A44 | H | H | 4,5-di-F-2-MeO-phenyl- | t-Bu—(CO)O— | 1.22 (s, 9H), 3.74 (s, 3H), 4.94 (m, 2H), 6.23 (tt, 1H), 6.81 (dd, 1H), 7.07 (t, 1H), 8.51 (d, 1H), 8.55 (d, 1H). |
| A45 | H | H | 2-Et-phenyl- | i-Pr—(CO)O— | 1.01 (d, 3H), 1.06 (d, 3H), 1.16 (t, 3H), 2.40-2.59 (m, 2H), 2.67-2.74 (m, 1H), 4.91-5.02 (m, 2H), 6.26 (tt, 1H), 7.11 (d, 1H), 6.26 (tt, 7.26 (m, 1H), 7.34-7.39 (m, 2H), 8.54 (d, 1H), 8.59 (d, 1H). |
| A46 | H | H | 2,3-di-Cl-phenyl- | i-Pr—(CO)O— | 1.08 (d, 3H), 1.15 (d, 3H), 2.76 (m, 1H), 4.95 (dt, 2H), 6.25 (tt, 1H), 7.19 (dd, 1H), 7.28 (t, 1H), 7.54 (dd, 1H), 8.55 (d, 1H), 8.60 (d, 1H). |
| A47 | H | H | 2-Cl-6-F₃C- | t-Bu—(CO)O— | 1.10 (s, 9H), 4.97 (m, 2H), 6.22 (tt, 1H), 7.51 (t, 1H), |

TABLE A-continued

Compounds of formula (Ia''), i.e. compounds of formula (I) wherein $R^3$ is 2,2-difluoro-ethyl, and $R^1$, $R^2$, $R^4$ and $R^5$ have the values as defined in the table below.

(Ia'')

| Compound No | $R^1$ | $R^2$ | $R^4$ | $R^5$ | $^1$H-NMR (400 MHz, CDCl$_3$ unless indicated otherwise) |
|---|---|---|---|---|---|
| | | | phenyl- | | 7.71 (d, 2H), 8.55 (d, 1H), 8.60 (d, 1H). |
| A48 | H | H | 2,3-di-Cl-6-F-phenyl | i-Pr—(CO)O— | 1.20 (m, 6H), 2.82 (m, 1H), 4.98 (m, 2H), 6.12 (tt, 1H), 7.03 (t, 1H), 7.50 (m, 1H), 8.52 (d, 1H), 8.60 (d, 1H). |

Key:
s = singlet;
d = doublet;
t = triplet;
dd = double doublet;
ddd = double double doublet;
dt = double triplet;
tt = triple triplet;
q = quartet;
sept = septet;
m = multiplet;
Me = methyl;
Et = ethyl;
Pr = propyl;
Bu = butyl;
Ph = phenyl.

TABLE B

Compounds of formula (Ib''), i.e. compounds of formula (I) wherein $R^1$ and $R^2$ are hydrogen, $R^3$ is 2,2-difluoro-ethyl, $R^5$ is hydroxy, and $R^4$ has the values as defined in the table below.

(Ib'')

| Compound No | $R^4$ | $^1$H-NMR (400 MHz, CDCl$_3$ unless indicated otherwise) |
|---|---|---|
| B1 | 2-Cl-3-F$_3$C-phenyl- | 5.00 (m, 2H), 6.30 (tt, 1H), 7.05 (m, 2H), 7.21 (m, 1H), 8.60 (d, 1H), 8.78 (d, 1H). |
| B2 | 2-Cl-3,6-di-F-phenyl- | 4.92 (dt, 2H), 6.09-6.40 (tt, 1H), 7.08-7.14 (m, 2H), 7.16-7.26 (m, 2H), 8.52 (d, 1H), 8.72 (d, 1H). |
| B3 | 2-Cl-5-F$_3$C-phenyl- | 4.92 (m, 2H), 6.94 (tt, 1H), 7.59-7.67 (m, 3H), 8.51 (d, 1H), 8.71 (d, 1H). |
| B4 | 2,6-di-Et-4-Me- | 1.00 (d, 3H), 1.10 (t, 3H), 2.34-2.42 (m, 2H), 2.36 (s, |

TABLE B-continued

Compounds of formula (Ib''), i.e. compounds of formula (I) wherein $R^1$ and $R^2$ are hydrogen, $R^3$ is 2,2-difluoro-ethyl, $R^5$ is hydroxy, and $R^4$ has the values as defined in the table below.

(Ib'')

| Compound No | $R^4$ | $^1$H-NMR (400 MHz, CDCl$_3$ unless indicated otherwise) |
|---|---|---|
| | phenyl- | 3H), 2.63-2.73 (m, 1H), 4.98 (dt, 2H), 6.25 (tt, 1H), 6.99 (s, 2H), 8.52 (d, 1H), 8.57 (d, 1H). |
| B5 | 2,4,6-tri-Me-phenyl- | 2.11 (s, 6H), 2.31 (s, 3H), 4.92 (dt, 2H), 6.24 (tt, 1H), 6.98 (s, 2H), 7.87 (s, 1H), 8.48 (d, 1H), 8.65 (d, 1H). |
| B6 | 3-Br-2-Cl-6-F-phenyl- | 4.92 (dt, 2H), 6.23 (tt, 1H), 7.03 (t, 1H), 7.69 (dd, 1H), 8.26 (s, 1H), 8.51 (d, 1H), 8.71 (d, 1H). |
| B7 | 2-Cl-5-F-phenyl- | 4.91 (m, 2H), 6.24 (tt, 1H), 7.10 (m, 2H), 7.48 (dd, 1H), 8.16 (s, 1H), 8.50 (d, 1H), 8.69 (d, 1H). |
| B8 | 2-MeO-5-F$_3$CO-phenyl- | 3.85 (s, 3H), 4.90 (m, 2H), 6.24 (tt, 1H), 7.08 (d, 1H), 7.60 (s, 1H), 7.66 (d, 1H), 8.07 (s, 1H), 8.47 (d, 1H), 8.66 (d, 1H). |
| B9 | 2-Cl-6-F-3-O$_2$N-phenyl- | (CD$_3$OD): 4.80 (m, 2H), 6.18 (tt, 1H), 7.42 (m, 1H), 8.03 (m, 1H), 8.62 (d, 1H), 8.74 (d, 1H). |
| B10 | 5-Cl-2-F$_3$C-phenyl- | 4.89 (dt, 2H), 6.20 (tt, 1H), 7.37 (s, 1H), 7.52 (d, 1H), 7.73 (d, 1H), 8.50 (d, 1H), 8.70 (d, 1H). |
| B11 | 2,3,6-tri-Cl-phenyl- | (CD$_3$OD): 4.85 (m, 2H), 6.16 (m, 1H), 7.41 (d, 1H), 7.48 (d, 1H), 8.55 (d, 1H), 8.65 (d, 1H). |
| B12 | 5-Br-2-MeO-phenyl- | 3.78 (s, 3H), 4.90 (m, 2H), 6.23 (tt, 1H), 6.90 (d, 1H), 7.44 (d, 1H), 7.49 (dd, 1H), 8.47 (d, 1H), 8.65 (d, 1H). |
| B13 | 2-Cl-6-F$_3$C-phenyl- | 4.96 (dt, 2H), 6.20 (tt, 1H), 7.51 (t, 1H), 7.73 (d, 2H), 8.50 (d, 1H), 8.70 (d, 1H). |
| B14 | 2,3-di-Cl-6-F-phenyl- | 4.92 (2H, m), 6.25 (1H, m), 7.20 (1H, dd), 7.53 (1H, dd), 8.52 (1H, d), 8.71 (1H, d). |
| B15 | 2,3-di-Cl-phenyl- | 4.91 (m, 2H), 6.24 (tt, 1H), 7.31 (m, 2H), 7.54 (m, 1H), 8.50 (d, 1H), 8.69 (d, 1H). |

Key:
s = singlet;
d = doublet;
t = triplet;
dd = double doublet;
dt = double triplet;
tt = triple triplet;
m = multiplet;
Me = methyl;
Et = ethyl.

TABLE C

Compounds of formula (Ia'), i.e. compounds of formula (I) wherein $R^1$ and $R^2$ are hydrogen, and $R^3$, $R^4$ and $R^5$ have the values as defined in the table below.

(Ia')

| Compound No | $R^3$ | $R^4$ | $R^5$ | $^1$H-NMR (400 MHz, CDCl$_3$ unless indicated otherwise) |
|---|---|---|---|---|
| C1 | 4-chloro-butyl- | 2-F$_3$CO-phenyl- | t-Bu—(CO)O— | 1.17 (s, 9H), 1.83-2.00 (m, 4H), 3.57-3.63 (m, 2H), 4.52-4.60 (m, 2H), 7.31-7.40 (m, 3H), 7.42-7.49 (m, 1H), 8.48 (d, 1H), 8.56 (d, 1H). |
| C2 | 3,3,3-trifluoro-propyl- | 2-F$_3$CO-phenyl- | t-Bu—(CO)O— | 1.17 (s, 9H), 2.56-2.69 (m, 2H), 4.74-4.87 (m, 2H), 7.30-7.41 (m, 3H), 7.43-7.50 (m, 1H), 8.51 (d, 1H), 8.59 (d, 1H). |
| C3 | 4,4,4,3,3-penta-fluoro-butyl- | 2-F$_3$CO-phenyl- | t-Bu—(CO)O— | 1.18 (s, 9H), 2.50-2.66 (m, 2H), 4.80-4.93 (m, 2H), 7.33-7.41 (m, 3H), 7.44-7.51 (m, 1H), 8.52 (d, 1H), 8.60 (d, 1H). |
| C4 | 4-chloro-butyl- | 2-Cl-3,6-di-F-phenyl- | t-Bu—(CO)O— | 1.24 (s, 9H), 1.90-2.04 (m, 4H), 3.64 (t, 2H), 4.60 (t, 2H), 7.09-7.16 (m, 1H), |

TABLE C-continued

Compounds of formula (Ia'), i.e. compounds of formula (I) wherein $R^1$ and $R^2$ are hydrogen, and $R^3$, $R^4$ and $R^5$ have the values as defined in the table below.

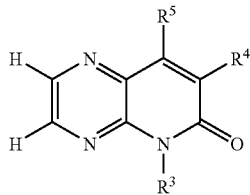

(Ia')

| Compound No | $R^3$ | $R^4$ | $R^5$ | $^1$H-NMR (400 MHz, CDCl$_3$ unless indicated otherwise) |
|---|---|---|---|---|
| | | | | 7.22-7.29 (m, 1H), 8.56 (d, 1H), 8.64 (d, 1H). |
| C5 | 3-chloro-propyl- | 2-Cl-3,6-di-F-phenyl- | t-Bu—(CO)O— | 1.24 (s, 9H), 2.29-2.38 (m, 2H), 3.69 (t, 2H), 4.72 (t, 2H), 7.09-7.16 (m, 1H), 7.22-7.29 (m, 1H), 8.57 (d, 1H), 8.65 (d, 1H). |
| C6 | 3,3,3-trifluoro-propyl- | 2-Cl-3,6-di-F-phenyl- | t-Bu—(CO)O— | 1.21 (s, 9H), 2.59-2.71 (m, 2H), 4.79-4.86 (m, 2H), 7.07-7.13 (m, 1H), 7.20-7.27 (m, 1H), 8.57 (d, 1H), 8.63 (d, 1H). |
| C7 | 4,4,4,3,3-penta-fluoro-butyl- | 2-Cl-3,6-di-F-phenyl- | t-Bu—(CO)O— | 1.21 (s, 9H), 2.53-2.68 (m, 2H), 4.84-4.90 (m, 2H), 7.07-7.14 (m, 1H), 7.21-7.27 (m, 1H), 8.58 (d, 1H), 8.64 (d, 1H). |
| C8 | 2,2,2-trifluoro-ethyl- | 2-Cl-3,6-di-F-phenyl- | t-Bu—(CO)O— | 1.21 (t, 9H), 5.28 (q, 2H), 7.07-7.28 (m, 2H), 8.58 (m, 1H), 8.61 (m, 1H). |
| C9 | 2-fluoro-ethyl- | 2-Cl-3,6-di-F-phenyl- | t-Bu—(CO)O— | 1.21 (s, 9H), 4.77 (t, 1H), 4.87-4.93 (m, 2H), 4.94-4.99 (m, 2H), 7.06-7.12 (m, 1H), 7.20-7.26 (m, 1H), 8.53 (d, 1H), 8.61 (d, 1H). |
| C10 | 2,2,2-trifluoro-ethyl- | 2-Cl-3,6-di-F-phenyl- | i-Pr—(CO)O— | 1.16-1.17 (d, 6H), 2.78-2.85 (m, 1H), 5.25-5.31 (m, 2H), 7.07-7.12 (m, 1H), 7.21-7.26 (m, 1H), 8.58 (d, 1H), 8.62 (d, 1H). |
| C11 | 4,4-difluoro-but-3-en-1-yl- | 2-Cl-3,6-di-F-phenyl- | t-Bu—(CO)O— | 1.20 (s, 9H), 2.51 (q, 2H), 4.21-4.32 (m, 1H), 4.59 (t, 2H), 7.06-7.12 (m, 1H), 7.19-7.27 (m, 1H), 8.52 (d, 1H), 8.60 (d, 1H). |
| C12 | 3,4,4-trifluoro-but-3-en-1-yl- | 2-Cl-3,6-di-F-phenyl- | t-Bu—(CO)O— | 1.20 (s, 9H), 2.78-2.89 (m, 2H), 4.79 (t, 2H), 7.06-7.12 (m, 1H), 7.19-7.27 (m, 1H), 8.54 (d, 1H), 8.62 (d, 1H). |
| C13 | 3,3-dichloro-prop-2-en-1-yl- | 2-Cl-3,6-di-F-phenyl- | t-Bu—(CO)O— | 1.21 (s, 9H), 5.28 (d, 2H), 6.06 (t, 1H), 7.06-7.12 (m, 1H), 7.19-7.26 (m, 1H), 8.55 (d, 1H), 8.62 (d, 1H). |
| C14 | 3,3-dichloro-prop-2-en-1-yl- | 2-Cl-3,6-di-F-phenyl- | i-Pr—(CO)O— | 1.17 (dd, 6H), 2.80 (sept, 1H), 5.28 (d, 2H), 6.07 (t, 1H), 7.07-7.12 (m, 1H), 7.20-7.26 (m, 1H), 8.55 (d, 1H), 8.63 (d, 1H). |
| C15 | 2-fluoro-prop-2-en-1-yl- | 2-Cl-3,6-di-F-phenyl- | t-Bu—(CO)O— | 1.20 (s, 9H), 4.47 (dd, 1H), 4.76 (dd, 1H), 5.29 (d, 2H), 7.05-7.12 (m, 1H), 7.19-7.25 (m, 1H), 8.55 (d, 1H), 8.61 (d, 1H). |
| C16 | 2-fluoro-prop-2-en-1-yl- | 2-Cl-3,6-di-F-phenyl- | i-Pr—(CO)O— | 1.17 (dd, 6H), 2.81 (sept, 1H), 4.49 (dd, 1H), 4.77 (dd, 1H), 5.29 (d, 2H), 7.06-7.12 (m, 1H), 7.20-7.26 (m, 1H), 8.55 (d, 1H), 8.62 (d, 1H). |
| C17 | 2-chloro-prop-2-en-1-yl- | 2-Cl-3,6-di-F-phenyl- | i-Pr—(CO)O— | 1.17 (dd, 6H), 2.81 (sept, 1H), 5.20 (d, 1H), 5.32 (s, 2H), 5.35 (d, 1H), 7.06-7.12 (m, 1H), 7.19-7.26 (m, 1H), 8.55 (d, 1H), 8.62 (d, 1H). |
| C18 | 3,3-difluoro-prop-2-en-1-yl- | 2-Cl-3,6-di-F-phenyl- | i-Pr—(CO)O— | 1.17 (dd, 6H), 2.81 (sept, 1H), 4.57-4.67 (m, 1H), 5.17 (d, 2H), 7.06-7.12 (m, 1H), 7.20-7.25 (m, 1H), 8.53 (d, 1H), 8.62 (d, 1H). |

Key:
s = singlet;
d = doublet;
t = triplet;
dd = double doublet;
q = quartet;
sept = septet;
m = multiplet;
Pr = propyl;
Bu = butyl.

TABLE D

Compounds of formula (Ib'), i.e. compounds of formula (I) wherein $R^1$ and $R^2$ are hydrogen, $R^5$ is hydroxy, and $R^3$ and $R^4$ have the values as defined in the table below.

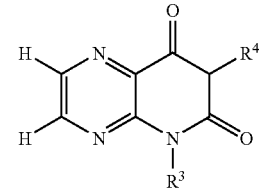

(Ib')

| Compound No | $R^3$ | $R^4$ | $^1$H-NMR (400 MHz, CDCl$_3$ unless indicated otherwise) |
|---|---|---|---|
| D1 | 2,2,2-trifluoro-ethyl- | 2-Cl-3,6-di-F-phenyl- | 5.27-5.34 (m, 2H), 7.21-7.26 (m, 1H), 7.35-7.41 (m, 1H), 8.70 (d, 1H), 8.78 (d, 1H). |
| D2 | 2-fluoro-ethyl- | 2-Cl-3,6-di-F-phenyl- | 4.74 (t, 1H), 4.83-4.88 (m, 2H), 4.89-4.95 (m, 1H), 7.06-7.13 (m, 1H), 7.18-7.25 (m, 1H), 8.48 (d, 1H), 8.70 (d, 1H). |
| D3 | 3,3-dichloro-prop-2-en-1-yl- | 2-Cl-3,6-di-F-phenyl- | (d$_6$-DMSO): 5.02 (d, 2H), 6.19 (t, 1H), 7.31-7.37 (m, 1H), 7.47-7.54 (m, 1H), 8.62 (d, 1H), 8.79 (d, 1H). |
| D4 | 3,3-difluoro- | 2-Cl-3,6-di-F- | (d$_6$-DMSO): 4.73-4.85 (m, 1H), 4.98 (d, 2H), 7.36-7.42 |

TABLE D-continued

Compounds of formula (Ib'), i.e. compounds of formula (I) wherein $R^1$ and $R^2$ are hydrogen, $R^5$ is hydroxy, and $R^3$ and $R^4$ have the values as defined in the table below.

(Ib')

| Compound No | $R^3$ | $R^4$ | $^1$H-NMR (400 MHz, CDCl$_3$ unless indicated otherwise) |
|---|---|---|---|
| | prop-2-en-1-yl- | phenyl- | (m, 1H), 7.53-7.60 (m, 1H), 8.69 (d, 1H), 8.86 (d, 1H). |

Key:
d = doublet;
t = triplet;
m = multiplet.

Biological Examples

Example B1

Herbicidal Action

Seeds of a variety of test species were sown in sterilised standard soil in seed trays each having 96 cells. After cultivation for 8 to 9 days cultivation (post-emergence) under controlled conditions in a climatic chamber (cultivation at 23/17° C., day/night; 13 hours light; 50-60% humidity), the plants were treated with an aqueous spray solution of 1000 mg/l of the active ingredient dissolved in 10% DMSO (dimethyl sulfoxide, CAS RN 67-68-5) as a solvent, equivalent to 1000 g/ha. The plants were grown in the climatic chamber after application at (24/19° C., day/night; 13 hours light; 50-60% humidity) and watered twice daily. After 9 days until the test was evaluated (10=total damage to plant, 0=no damage to plant)

TABLE B1

Application post-emergence

| Comp No. | Rate (g/ha) | STEME | NAAOF | AMARE | SOLNI |
|---|---|---|---|---|---|
| A1 | 1000 | 7 | 8 | 0 | 6 |
| A2 | 1000 | 9 | 9 | 4 | 6 |
| A3 | 1000 | 9 | 7 | 6 | 5 |
| A5 | 1000 | 7 | 5 | 4 | 2 |
| A6 | 1000 | 7 | 7 | 5 | 0 |
| A7 | 1000 | 8 | 7 | 4 | 5 |
| A8 | 1000 | 7 | 7 | 6 | 6 |
| B1 | 1000 | 5 | 6 | 0 | 6 |
| B2 | 1000 | 8 | 8 | 6 | 5 |
| C2 | 1000 | 0 | 0 | 0 | 4 |
| C4 | 1000 | 1 | 0 | 0 | 4 |
| C6 | 1000 | 3 | 0 | 0 | 1 |
| C7 | 1000 | 0 | 0 | 0 | 3 |

STEME = *Stellaria media*;
NAAOF = *Nasturtium officinale*;
AMARE = *Amaranthus retroflexus*;
SOLNI = *Solanum nigrum*.

Compound No. C1, C3 and C5 were tested using the same protocol and showed no damage or very little damage to the test plants under the test conditions.

Example B2

Herbicidal Action

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days, the test was evaluated (10=total damage to plant; 0=no damage to plant).

TABLE B2

Application post-emergence

| Comp No. | Rate (g/ha) | SOLNI | AMARE | SETFA | ECHCG | IPOHE |
|---|---|---|---|---|---|---|
| A9 | 1000 | 10 | 10 | 9 | 7 | — |
| A10 | 1000 | 9 | 10 | 3 | 4 | 5 |
| A11 | 1000 | 10 | 10 | 9 | 9 | 10 |
| A12 | 1000 | 10 | 3 | 10 | 9 | 9 |
| A13 | 1000 | 10 | 10 | 9 | 8 | 10 |
| A14 | 1000 | 10 | 10 | 9 | 7 | 10 |
| A15 | 1000 | 10 | 6 | 9 | 8 | 9 |
| A16 | 1000 | 10 | 8 | 8 | 3 | 7 |
| A17 | 1000 | 5 | 3 | 7 | 6 | 0 |
| A19 | 1000 | 10 | 10 | 8 | 7 | 9 |
| A20 | 1000 | 9 | 10 | 8 | 7 | 7 |
| A23 | 1000 | 10 | 10 | 9 | 8 | 9 |
| A25 | 1000 | 10 | 7 | 7 | 7 | 8 |
| A26 | 1000 | 5 | 10 | 2 | 2 | 5 |
| A27 | 1000 | 9 | 9 | 7 | 7 | 7 |
| A28 | 1000 | 10 | 9 | 3 | 1 | 8 |
| A32 | 1000 | 10 | 10 | 7 | 4 | 9 |
| A33 | 1000 | 10 | 10 | 7 | 4 | 7 |
| A34 | 1000 | 10 | 10 | 6 | 4 | 9 |
| A35 | 1000 | 5 | 0 | 5 | 3 | 2 |
| A37 | 1000 | 5 | 6 | 7 | 5 | 7 |
| A38 | 1000 | 9 | 10 | 8 | 6 | 6 |
| A41 | 1000 | 10 | 10 | 9 | 8 | 9 |
| A42 | 1000 | 10 | 10 | 7 | 6 | 9 |
| A43 | 1000 | 9 | 10 | 9 | 8 | 9 |
| A44 | 1000 | 10 | 9 | 9 | 7 | 6 |
| A45 | 1000 | 10 | 10 | 8 | 5 | 9 |
| B3 | 250 | 9 | 10 | 7 | 7 | 8 |
| B4 | 1000 | 10 | 7 | 9 | 8 | 10 |
| B5 | 1000 | 10 | 7 | 8 | 8 | 10 |
| B6 | 1000 | 10 | 10 | 8 | 8 | 10 |
| B7 | 1000 | 9 | 10 | 7 | 7 | 9 |
| B8 | 1000 | 9 | 10 | 9 | 9 | 9 |
| B9 | 1000 | 9 | 9 | 7 | 8 | 8 |
| B10 | 1000 | 10 | 10 | 9 | 9 | 10 |
| B11 | 1000 | 10 | 10 | 9 | 8 | 10 |
| B12 | 1000 | 9 | 9 | 6 | 6 | 6 |
| B13 | 1000 | 10 | 10 | 9 | 9 | 10 |
| B14 | 1000 | 10 | 10 | 7 | 6 | 10 |
| C8 | 1000 | 10 | 10 | 4 | 1 | 10 |
| C9 | 1000 | 4 | 7 | 0 | 0 | 5 |
| C10 | 1000 | 10 | 10 | 6 | 3 | 10 |
| C11 | 1000 | 2 | 5 | 0 | 0 | 0 |
| C12 | 1000 | 3 | 6 | 0 | 0 | 1 |
| C13 | 1000 | 3 | 0 | 0 | 0 | 1 |
| C14 | 1000 | 8 | 8 | 0 | 0 | 1 |
| D1 | 1000 | 10 | 10 | 6 | 5 | 10 |
| D2 | 1000 | 7 | 6 | 2 | 1 | 5 |
| D3 | 1000 | 7 | 9 | 3 | 0 | 7 |

SOLNI = *Solanum nigrum*;
AMARE = *Amaranthus retroflexus*;
SETFA = *Setaria faberi*;
ECHCG = *Echinochloa crus-galli*;
IPOHE = *Ipomea hederaceae*.

Compound No. A29, A30 and A31 were tested using the same protocol and showed no damage or very little damage to the test plants under the test conditions.

Example B3

Herbicidal Action

Seeds of a variety of test species were sown in sterilised compost in small pots. After cultivation for seven days (post-emergence) in controlled conditions in the glasshouse (at 24/16° C., day/night; 14 hours light; 65% humidity) the plants were sprayed with 1 mg of the active ingredient, formulated in 2.5 ml acetone/water (50:50) solution, which is equivalent to 1000 g/ha. Once the foliage was dry, the pots were kept in the glasshouse (at 24/16° C., day/night; 14 hours light; 65% humidity), and were watered twice daily. After 13 days the test was evaluated (10=total damage to plant, 0=no damage to plant).

TABLE B3

Application post-emergence

| Comp No. | Rate (g/ha) | AMARE | ALOMY | DIGSA | CHEAL |
|---|---|---|---|---|---|
| A4 | 1000 | 10 | 0 | 7 | 10 |
| A36 | 1000 | 10 | 8 | 5 | 10 |

AMARE = *Amaranthus retroflexus*;
ALOMY = *Alopecurus myosuroides*;
DIGSA = *Digitaria sanguinalis*;
CHEAL = *Chenopodium album*.

The invention claimed is:
1. A compound of formula (I)

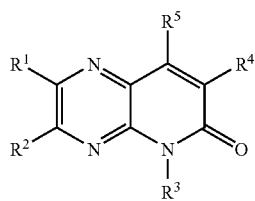

wherein
$R^1$ and $R^2$ are independently hydrogen, $C_1$-$C_4$alkyl, $C_1$-$C_4$haloalkyl, halo, cyano, hydroxy, $C_1$-$C_4$alkoxy, $C_1$-$C_4$alkylthio, aryl or aryl substituted by one to five $R^6$, which may be the same or different, or heteroaryl or heteroaryl substituted by one to five $R^6$, which may be the same or different;
$R^3$ is $C_1$-$C_4$haloalkyl, $C_2$-$C_4$haloalkenyl or $C_2$-$C_4$haloalkynyl;
$R^4$ is aryl or aryl substituted by one to five $R^8$, which may be the same or different, or heteroaryl or heteroaryl substituted by one to four $R^8$, which may be the same or different;
$R^5$ is hydroxy or a group which can be metabolised to the hydroxy group which is $R^9$-oxy-, $R^{10}$-carbonyloxy-, tri-$R^{11}$-silyloxy- or $R^{12}$-sulfonyloxy-;
and wherein:
each $R^6$ and $R^8$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, $C_1$-$C_{10}$alkylcarbonylamino-, aryl or aryl substituted by one to three $R^{13}$, which may be the same or different, heteroaryl or heteroaryl substituted by one to three $R^{13}$, which may be the same or different, aryl-$C_1$-$C_4$alkyl- or aryl-$C_1$-$C_4$alkyl- wherein the aryl moiety is substituted by one to three $R^{13}$, which may be the same or different, heteroaryl-$C_1$-$C_4$alkyl- or heteroaryl-$C_1$-$C_4$alkyl- wherein the heteroaryl moiety is substituted by one to three $R^{13}$, which may be the same or different, aryloxy- or aryloxy-substituted by one to three $R^{13}$, which may be the same or different, heteroaryloxy- or heteroaryloxy-substituted by one to three $R^{13}$, which may be the same or different, arylthio- or arylthio-substituted by one to three $R^{13}$, which may be the same or different, or heteroarylthio- or heteroarylthio-substituted by one to three $R^{13}$, which may be the same or different; and
each $R^{13}$ is independently halo, cyano, nitro, $C_1$-$C_6$alkyl, $C_1$-$C_6$haloalkyl or $C_1$-$C_6$alkoxy;
$R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy;
$R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, $C_1$-$C_{10}$alkylthio-, N-$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy -or aryloxy-substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio -or heteroarylthio-substituted by one to three $R^{14}$, which may be the same or different;
each $R^{11}$ is independently $C_1$-$C_{10}$alkyl or phenyl or phenyl substituted by one to five substituents independently selected from halo, cyano, nitro, $C_1$-$C_6$alkyl, $C_1$-$C_6$haloalkyl or $C_1$-$C_6$alkoxy;
$R^{12}$ is $C_1$-$C_{10}$alkyl, $C_1$-$C_{10}$haloalkyl, or phenyl or phenyl substituted by one to five substituents independently selected from halo, cyano, nitro, $C_1$-$C_6$alkyl, $C_1$-$C_6$haloalkyl or $C_1$-$C_6$alkoxy; and
each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy;
or a salt thereof.

2. A compound according to claim 1 wherein $R^4$ is aryl or aryl substituted by one to five $R^8$, which may be the same or different.

3. A compound according to claim 2, wherein $R^4$ is phenyl substituted by one to four $R^8$, which may be the same or different.

4. A compound according to claim 3, wherein $R^4$ is phenyl substituted by two to three $R^8$, which may be the same or different.

5. A compound according to claim 4, wherein $R^4$ is 2,5-bis-(trifluoromethyl)-phenyl, 3-bromo-2-chloro-6-fluoro-phenyl, 2-chloro-3,6-difluoro-phenyl, 2-chloro-5-fluoro-phenyl, 2-chloro-5-trifluoromethyl-phenyl, 2-chloro-6-trifluoromethyl-phenyl, 2,3-dichloro-6-fluoro-phenyl, 2,6-dichloro-phenyl, 2,6-dichloro-4-trifluoromethoxy-phenyl or 2,3,6-trichloro-phenyl.

6. A compound according to claim 4, wherein $R^4$ is 3-bromo-2-chloro-6-fluoro-phenyl.

7. A compound according to claim 3, wherein $R^4$ is 2,5-bis-(trifluoromethyl)-phenyl, 3-bromo-2-chloro-6-fluoro-phenyl, 2-chloro-3,6-difluoro-phenyl, 2-chloro-4-fluoro-phenyl, 2-chloro-5-fluoro-phenyl, 2-chloro-phenyl, 2-chloro-3-trifluoromethyl-phenyl, 2-chloro-5-trifluoromethyl-phenyl, 2-chloro-6-trifluoromethyl-phenyl, 2,3-dichloro-6-fluoro-phenyl, 2,4-dichloro-5-fluoro-phenyl, 3,5-dichloro-2-methoxy-phenyl, 2,3-dichloro-phenyl, 2,4-dichloro-phenyl, 2,5-dichloro-phenyl, 2,6-dichloro-phenyl, 2,6-dichloro-4-trifluoro-methoxy-phenyl, 2,6-dichloro-4-trifluoromethyl-phenyl, 2,6-diethyl-4-methyl-phenyl, 2,3-dimethoxy-phenyl, 2-fluoro-phenyl, 2-methoxy-phenyl, 2-methoxy-5-trifluoromethoxy-phenyl, 2,3,6-trichloro-phenyl, 2-trifluoromethoxy-phenyl, 2-trifluoromethyl-phenyl or 2,4,6-trimethyl-phenyl.

8. A compound according to claim 2, wherein $R^4$ is 2,5-bis-(trifluoromethyl)-phenyl, 3-bromo-2-chloro-6-fluoro-phenyl, 2-bromo-4-fluoro-phenyl, 5-bromo-2-methoxy-phenyl, 2-bromo-phenyl, 2-bromo-4-trifluoromethyl-phenyl, 2-chloro-3,6-difluoro-5-nitro-phenyl, 2-chloro-3,6-difluoro-phenyl, 2-chloro-4,5-difluoro-phenyl, 2-chloro-6-fluoro-3-methyl-phenyl, 2-chloro-6-fluoro-5-methyl-phenyl, 2-chloro-6-fluoro-3-nitro-phenyl, 2-chloro-4-fluoro-phenyl, 2-chloro-5-fluoro-phenyl, 2-chloro-6-fluoro-phenyl, 2-chloro-phenyl, 3-chloro-phenyl, 4-chloro-phenyl, 2-chloro-3-trifluoromethyl-phenyl, 2-chloro-5-trifluoromethyl-phenyl, 5-chloro-2-trifluoromethyl-phenyl, 2-chloro-6-trifluoromethyl-phenyl, 2,3-dichloro-6-fluoro-phenyl, 2,4-dichloro-5-fluoro-phenyl, 3,5-dichloro-2-methoxy-phenyl, 2,3-dichloro-phenyl, 2,4-dichloro-phenyl, 2,5-dichloro-phenyl, 2,6-dichloro-phenyl, 3,4-dichloro-phenyl, 2,6-dichloro-4-trifluoromethoxy-phenyl, 2,6-dichloro-4-trifluoromethyl-phenyl, 2,6-diethyl-4-methyl-phenyl, 2-difluoromethoxy-phenyl, 4,5-difluoro-2-methoxy-phenyl, 2,3-dimethoxy-phenyl, 2,4-dimethoxy-phenyl, 2,5-dimethyl-phenyl, 2-ethyl-phenyl, 2-fluoro-phenyl, 4-fluoro-2-trifluoromethyl-phenyl, 6-fluoro-2-trifluoromethyl-phenyl, 2-iodo-phenyl, 2-methoxy-phenyl, 2-methoxy-5-trifluoromethoxy-phenyl, 6-methyl-2-nitro-phenyl, 2-methyl-phenyl, naphth-2-yl, naphth-3-yl, phenyl, 2-nitro-4-trifluoromethyl-phenyl, 2,3,5-trichloro-phenyl, 2,3,6-trichloro-phenyl, 2-trifluoromethoxy-phenyl, 2-trifluoromethyl-phenyl, 2,3,6-trifluoro-phenyl or 2,4,6-trimethyl-phenyl.

9. A compound according to claim 1 wherein $R^3$ is $C_1$-$C_4$haloalkyl or $C_2$-$C_4$haloalkenyl.

10. A compound according to claim 9, wherein $R^3$ is $C_1$-$C_3$haloalkyl, where the halogen atoms are fluorine.

11. A compound according to claim 10 wherein $R^3$ is 2-fluoro-ethyl, 2,2-difluoro-ethyl, 2,2,2-trifluoro-ethyl or 3,3,3-trifluoro-propyl.

12. A compound according to claim 1, wherein $R^1$ is hydrogen, $C_1$-$C_4$alkyl, $C_1$-$C_4$haloalkyl, halo, cyano, hydroxy or $C_1$-$C_4$alkoxy.

13. A compound according to claim 12 wherein $R^3$ is 2,2-difluoro-ethyl.

14. A compound according to claim 1 wherein $R^5$ is hydroxy, $C_1$-$C_4$alkylcarbonyloxy-, $C_3$-$C_6$cycloalkylcarbonyloxy-, $C_2$-$C_4$alkenylcarbonyloxy-, $C_2$-$C_4$alkynylcarbonyloxy-, $C_1$-$C_4$alkoxycarbonyloxy-, $C_2$-$C_4$alkenyloxycarbonyloxy-, $C_2$-$C_4$alkynyloxycarbonyloxy- or $C_1$-$C_4$alkylthiocarbonyloxy-.

15. A compound according to claim 14, wherein $R^5$ is hydroxy, $C_1$-$C_4$alkylcarbonyloxy-, $C_1$-$C_4$alkoxycarbonyloxy- or $C_1$-$C_4$alkylthiocarbonyloxy-.

16. A compound according to claim 1 wherein $R^2$ is hydrogen, $C_1$-$C_4$alkyl, $C_1$-$C_4$haloalkyl, halo, cyano, hydroxy or $C_1$-$C_4$alkoxy.

17. A compound according to claim 1 wherein each $R^6$ is independently halo, $C_1$-$C_4$alkyl, $C_1$-$C_4$haloalkyl, $C_1$-$C_4$alkoxy or $C_1$-$C_4$haloalkoxy.

18. A compound according to claim 1 wherein each $R^8$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl- or $C_1$-$C_4$haloalkylsulfonyl-.

19. A compound according to claim 1 wherein $R^9$ is $C_2$-$C_{10}$alkenyl, $C_2$-$C_{10}$alkynyl, aryl-$C_1$-$C_4$alkyl- or aryl-$C_1$-$C_4$alkyl- wherein the aryl moiety is phenyl substituted by one to three $R^{13}$, which may be the same or different.

20. A compound according to claim 1 wherein $R^{10}$ is $C_1$-$C_{10}$alkyl, $C_3$-$C_{10}$cycloalkyl, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_1$-$C_{10}$ alkylthio-, N-$C_1$-$C_4$alkyl-amino-, N,N-di-($C_1$-$C_4$alkyl)-amino-, phenyl or phenyl substituted by one to three $R^{14}$, which may be the same or different, benzyl or benzyl wherein the phenyl moiety is substituted by one to three $R^{14}$, which may be the same or different, thienyl or thienyl substituted by one to three $R^{14}$, which may be the same or different, pyridyl or pyridyl substituted by one to three $R^{14}$, which may be the same or different, phenoxy or phenoxy substituted by one to three $R^{14}$, which may be the same or different, or phenylthio or phenylthio substituted by one to three $R^{14}$, which may be the same or different.

21. A compound according to claim 1 wherein each $R^{11}$ is independently $C_1$-$C_4$alkyl.

22. A compound according to claim 1 wherein $R^{12}$ is $C_1$-$C_4$alkyl or $C_1$-$C_4$haloalkyl.

23. A compound according to claim 1 wherein each $R^{13}$ is independently halo, nitro, $C_1$-$C_4$alkyl, $C_1$-$C_4$haloalkyl or $C_1$-$C_4$alkoxy.

24. A compound according to claim 1 wherein each $R^{14}$ is independently halo, nitro, $C_1$-$C_4$alkyl, $C_1$-$C_4$haloalkyl, $C_1$-$C_4$alkoxy or $C_1$-$C_4$haloalkoxy.

25. A compound according to claim 1, wherein $R^1$ is hydrogen, methyl, chloro or bromo, and $R^2$ is hydrogen, methyl, chloro or bromo.

26. A compound according to claim 1, wherein:
aryl is phenyl;
heteroaryl is selected from pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl; and
heterocyclyl is selected from heteroaryl, piperidinyl, 1,3-dioxolanyl, 1,3-dioxanyl, 4,5-dihydro-isoxazolyl, tetrahydrofuranyl and morpholinyl.

27. A herbicidal composition which comprises a herbicidally effective amount of a compound of formula (I) as defined in claim 1 in addition to formulation adjuvants.

28. A method of controlling plants which comprises applying to the plants or to the locus thereof a herbicidally effective amount of a compound of formula (I) as defined in claim 1.

* * * * *